United States Patent
Giuliani et al.

(10) Patent No.: US 9,498,429 B2
(45) Date of Patent: Nov. 22, 2016

(54) USE OF A VEGETAL EXTRACT FOR THE PREVENTION AND TREATMENT OF HAIR LOSS

(71) Applicant: GIULIANI S.P.A., Milan (IT)

(72) Inventors: Giammaria Giuliani, Milan (IT); Anna Benedusi, Milan (IT); Barbara Marzani, Carbonara al Ticino (IT)

(73) Assignee: GIULIANI S.P.A., Milan (IT)

( * ) Notice: Subject to any disclaimer, the term of this patent is extended or adjusted under 35 U.S.C. 154(b) by 0 days.

(21) Appl. No.: 15/031,937

(22) PCT Filed: Oct. 28, 2014

(86) PCT No.: PCT/IB2014/065655
§ 371 (c)(1),
(2) Date: Apr. 25, 2016

(87) PCT Pub. No.: WO2015/063678
PCT Pub. Date: May 7, 2015

(65) Prior Publication Data
US 2016/0296462 A1    Oct. 13, 2016

(30) Foreign Application Priority Data
Oct. 28, 2013 (IT) .............................. MI2013A1792

(51) Int. Cl.
*A01N 65/00* (2009.01)
*A61K 8/97* (2006.01)
*A61Q 7/00* (2006.01)

(52) U.S. Cl.
CPC . *A61K 8/97* (2013.01); *A61Q 7/00* (2013.01); *A61K 2800/92* (2013.01)

(58) Field of Classification Search
CPC ..................................................... A61K 36/00
USPC ........................................................ 424/725
See application file for complete search history.

(56) References Cited

PUBLICATIONS

Sendula M: "Cosmetic plant extract product for hair and skin regeneration", WPI / Thomson,, vol. 2000, No. 36, May 28, 2000.*

* cited by examiner

*Primary Examiner* — Michael Meller
(74) *Attorney, Agent, or Firm* — Abelman, Frayne & Schwab

(57) ABSTRACT

The present invention relates, in one aspect, to the use of a composition based on a vegetal extract of *Galeopsis segetum* Necker and of a physiologically acceptable carrier in the treatment or prevention of hair loss. The composition finds application in the field of trichology and may be applied topically on the scalp or administered orally.

11 Claims, 10 Drawing Sheets

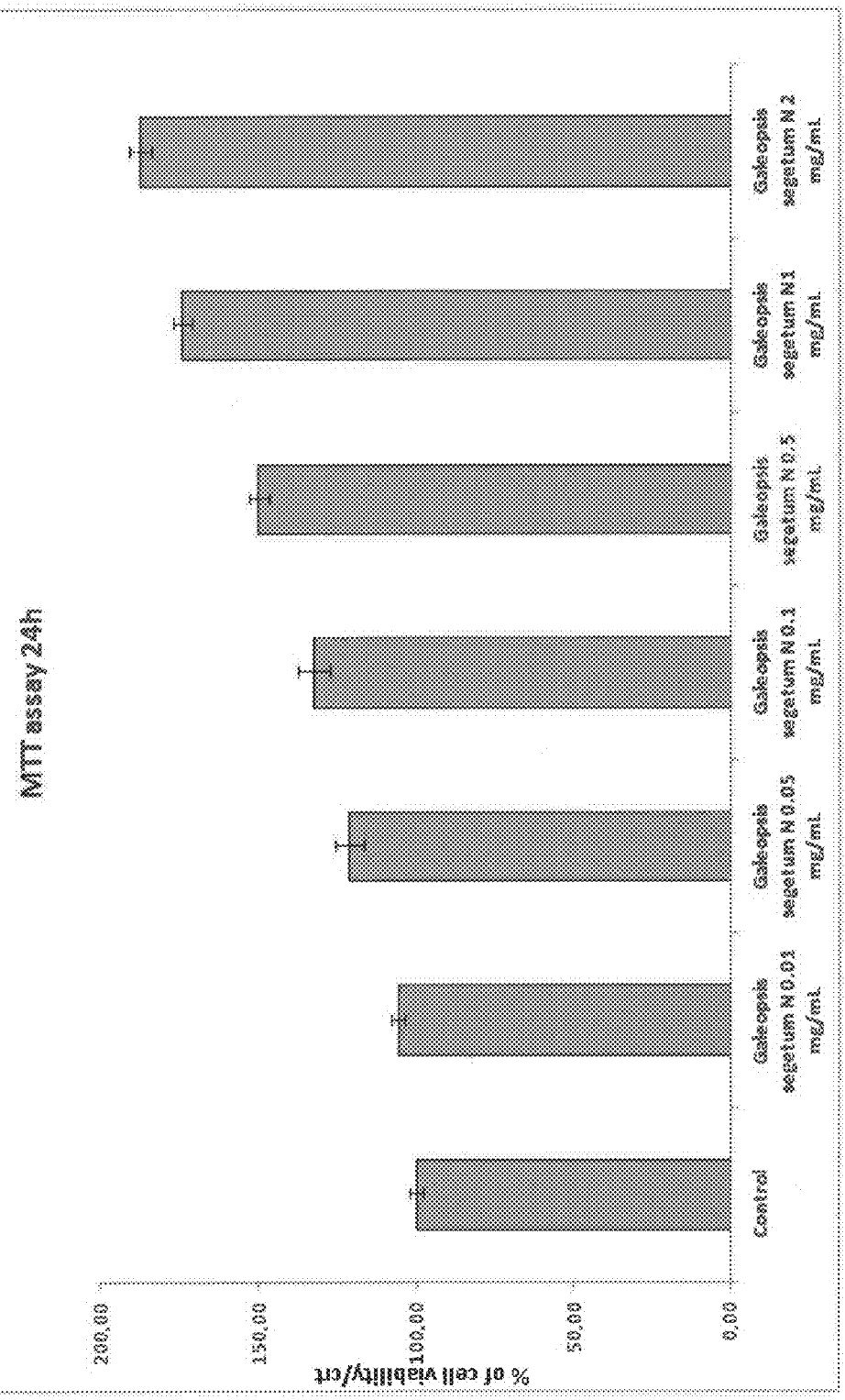

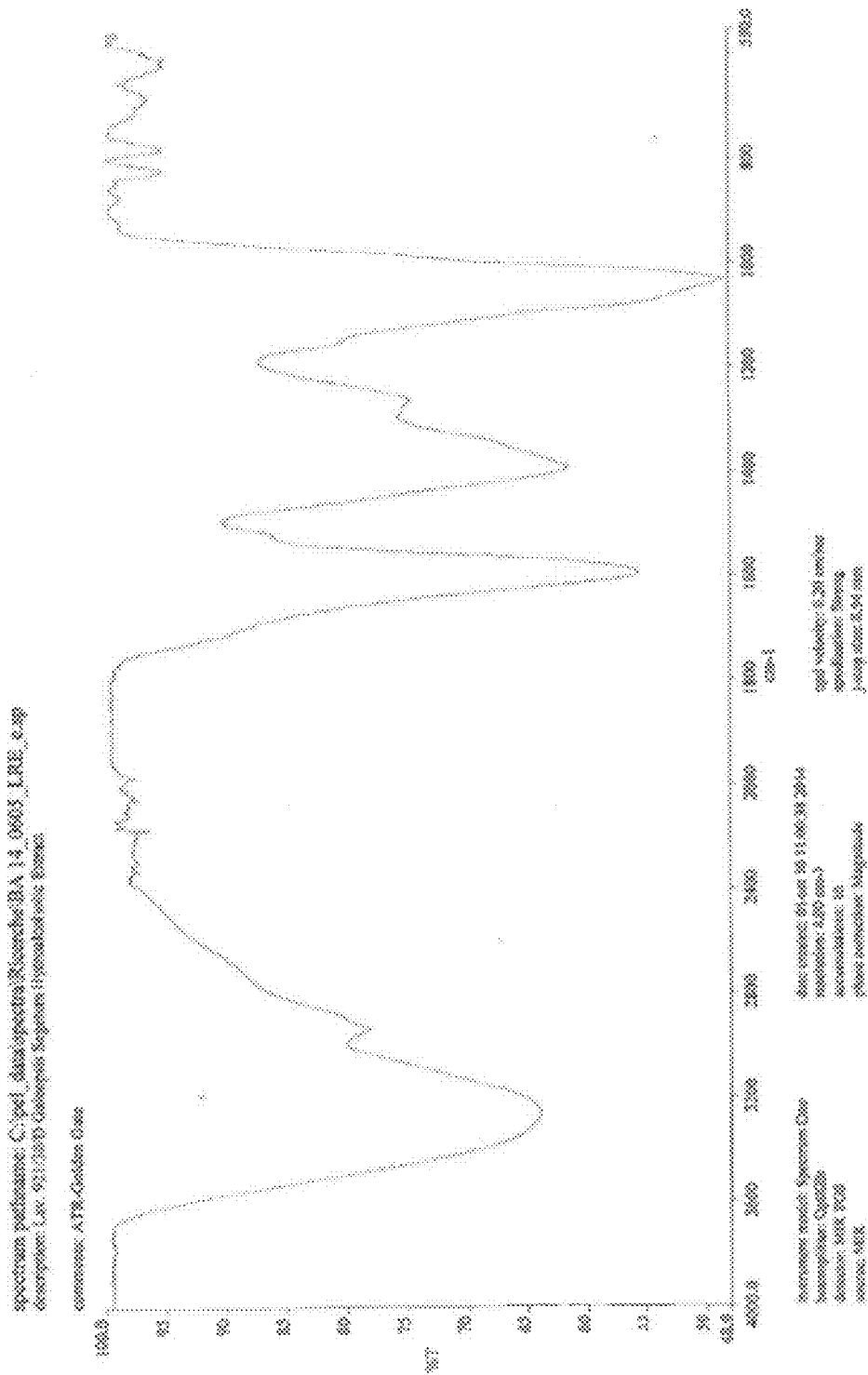

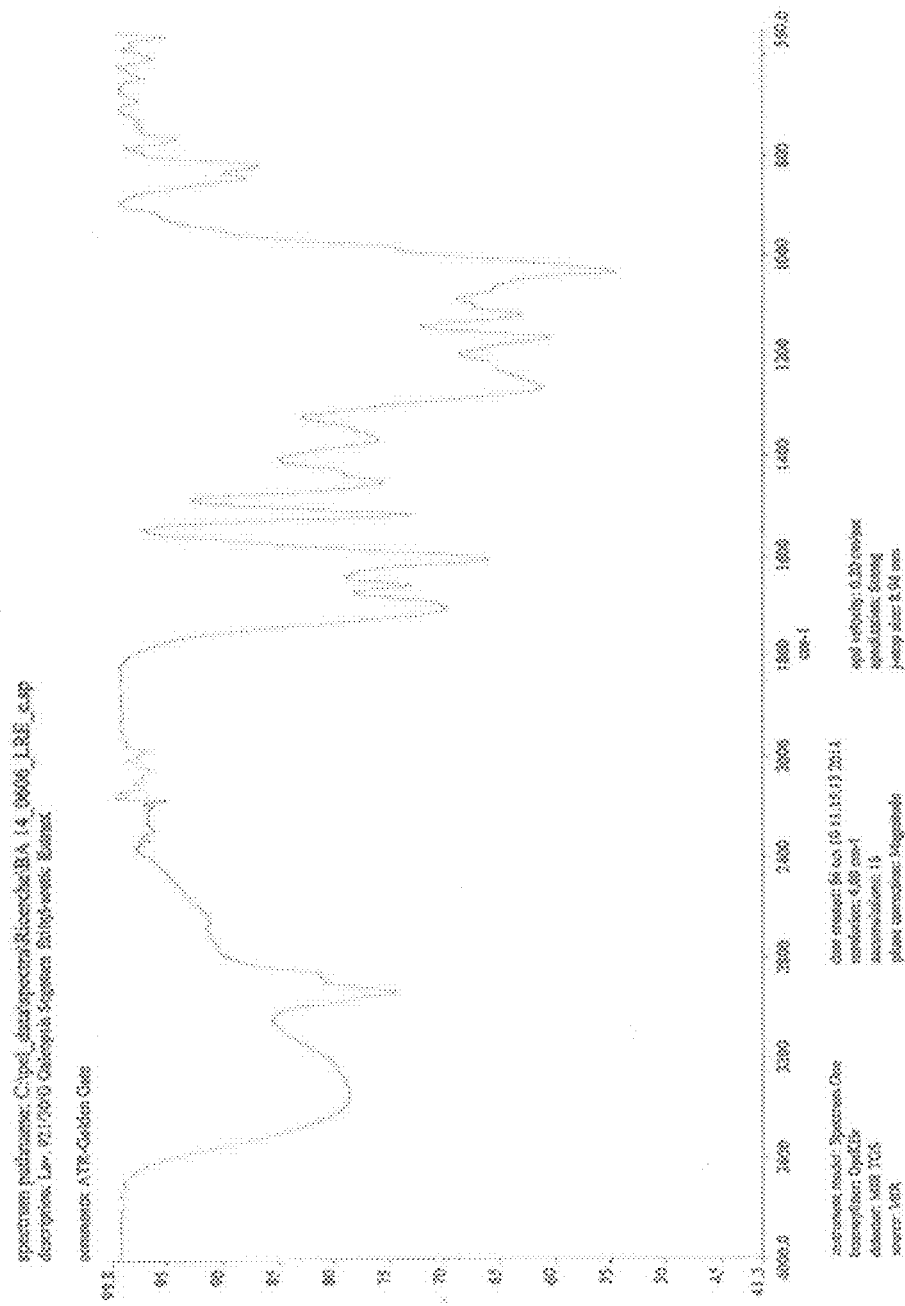

USE OF A VEGETAL EXTRACT FOR THE PREVENTION AND TREATMENT OF HAIR LOSS

FIELD OF THE INVENTION

The present invention relates to the use of a vegetal extract for the prevention and treatment of hair loss.

The present invention originates in the field of trichology and of nutritional or dietary products.

In particular the present invention relates to the use of a vegetal extract for stimulating the physiological growth of hair in the areas affected by thinning and/or baldness.

BACKGROUND ART

Hair have a protecting role and are considered as a skin annex along with sebaceous glands, sudoriferous glands and nails. Hair have a unique and peculiar feature: cyclicity.

The life cycle of the hair bulb is essentially represented by three subsequent phases: anagen (growth), catagen (involution) and telogen (rest phase).

The period of hair growth is followed by a regression phase, during which the deepest part of the follicle undergoes programmed cell death.

At the end of this phase, the cycle restarts. The biological phases of this phenomenon reside in the capability of stem cells of the bulb to leave, at alternating steps, their state of quiescence. During the bulb growth and hair production phase the proliferation, differentiation and survival activities are prevailing which are regulated by growth factors. The regression phase, on the contrary, is characterized by the activation of molecular pathways that induce apoptosis in bulb cells.

If the role of hair is considered in social relations, hair loss may be hard to face for many people.

In the anagen phase, the dermal papilla generates chemical signals that activate and instruct the stem cells of the bulge which by migrating to the base of the follicle form the hair matrix. With this "migration" the stem cells of the bulge create a "path" of cells which will give rise to the outer root sheath or ORS.

In response to further signals by the dermal papilla, the matrix cells, which derive from stem cells, proliferate and start the differentiation process, by moving upwards to form the shaft and inner sheath of the hair follicle.

The start of catagen is characterized by the end of cell proliferation and the apoptosis of matrix cells. During catagen the dermal papilla migrates towards the lowermost portion of the bulge. This close proximity of the papilla to the bulge is believed to be essential for initiating another hair production cycle. This enables interaction/activation of bulge cells at rest and a new cycle of hair growth.

Upon catagen/telogen transition, some cells of the bulge migrate to meet the papilla, generating the hair germ.

Hair in telogen contains a cell population at its base, which is in fact called hair germ, located in close proximity to the dermal papilla. The hair germ is activated to proliferate towards the end of the telogen phase, even before the bulge, to form, by surrounding the papilla, the matrix of the new bulb.

Different factors, among which stress, the lack of nutrients and ageing, negatively affect the life cycle of the hair bulb, determining a reduction of the number of hair and their thinning.

In individuals suffering from androgenetic alopecia (AGA), over time the follicles, which are formed again at the beginning of the new anagen phase, become smaller in size, leading to the formation of hair with smaller diameter as compared to the initial diameter. As a consequence, the formation of microscopic hair occurs. It was observed that although the follicles of scalp atrophy, there still remains a supply of stem cells which convert to progenitor cells, even though to a lesser extent as compared to the scalp in physiological conditions.

Most of the hair preparations available on the market target hair bulbs and act on scalp metabolism, feeding, oxygenation and microcirculation improving the conditions contributing to a physiological growth of hair.

Different products and treatments are available on the market to treat and prevent hair loss. However, the use of those products that to date have shown to be particularly effective in treating hair loss, such as minoxidil or some anti-steroidal drugs of a synthetic origin, is not free from drawbacks. Specifically, the topical use of minoxidil may determine the occurrence of side effects of a certain degree such as skin rashes, local inflammations, cephalea, while the oral administration of drugs such as finasteride may determine the appearance of hormonal dysfunctions with potential negative effects on sex life.

Other products currently used in the trichological field, in spite of being based on products of a natural origin, on the contrary, have the drawback of being made through complex preparation processes and, therefore, are particularly expensive. Consequently, there is currently a need to provide products containing substances that are active in stimulating the physiological process of hair growth and the use of which does not cause significant side effects.

One of the objects of the invention is to provide a composition or preparation containing active agents of a non-synthetic origin which are suitable for stimulating the physiological hair growth in subjects suffering from hair loss or thinning and the use of which is nearly free from significant side effects.

Another object of the invention is to provide a composition for trichological use which may be applied locally or administered orally, the active agents of which are of a vegetal origin obtainable via simple methods.

SUMMARY OF THE INVENTION

In the technical field of the invention, the Applicant has found that a vegetal extract obtained from a selected herbaceous plant stimulates the physiological process of hair growth when applied locally on the scalp or when administered orally.

In particular the Applicant has unexpectedly found that the plant of *Galeopsis segetum* Necker contains one or more active ingredients that stimulate the activity of the hair bulb and contribute to restoring the physiological conditions of hair growth.

In accordance with a first aspect of the invention, therefore, there is provided the use of a vegetal extract of *Galeopsis segetum* Necker for stimulating the physiological growth of hair.

In accordance with a second aspect, the invention provides a vegetal extract of *Galeopsis segetum* Necker for use in the treatment or prevention of hair loss. Surprisingly it has been observed that the vegetal extract of *Galeopsis segetum* Necker administered topically or orally in a subject suffering from hair thinning, determines a progressive thickening of thinner areas of the scalp.

In accordance with a third aspect, the present invention provides the use of a composition comprising a vegetal extract of *Galeopsis segetum* Necker and a physiologically acceptable carrier for stimulating the physiological growth of hair.

In accordance with a fourth aspect, a composition is provided comprising a vegetal extract of *Galeopsis segetum* Necker and a physiologically acceptable carrier for use in the treatment or prevention of hair loss.

Typically, the composition of the invention contains a trichologically active amount of one or more active ingredients present in the extract of *Galeopsis segetum* Necker.

BRIEF DESCRIPTION OF THE FIGURES

The features and advantages of the present invention will become more apparent from the appended drawing tables, wherein:

FIG. 6 shows bar graphs relating to an MTT assay at 24 hours demonstrating the percentage of cell activity as compared to a control determined by the treatment with vegetal extracts containing increasing amounts of *Galeopsis segetum* Necker, in accordance with Example 7.

FIG. 9 shows a graph with FT-IR spectrum of the hydroalcoholic extract of *Galeopsis Segetum* of Example 9;

FIG. 10 shows a graph with FT-IR spectrum of the ethyl acetic extract of *Galeopsis Segetum* of Example 9;

DETAILED DESCRIPTION OF THE INVENTION

Figure 1:
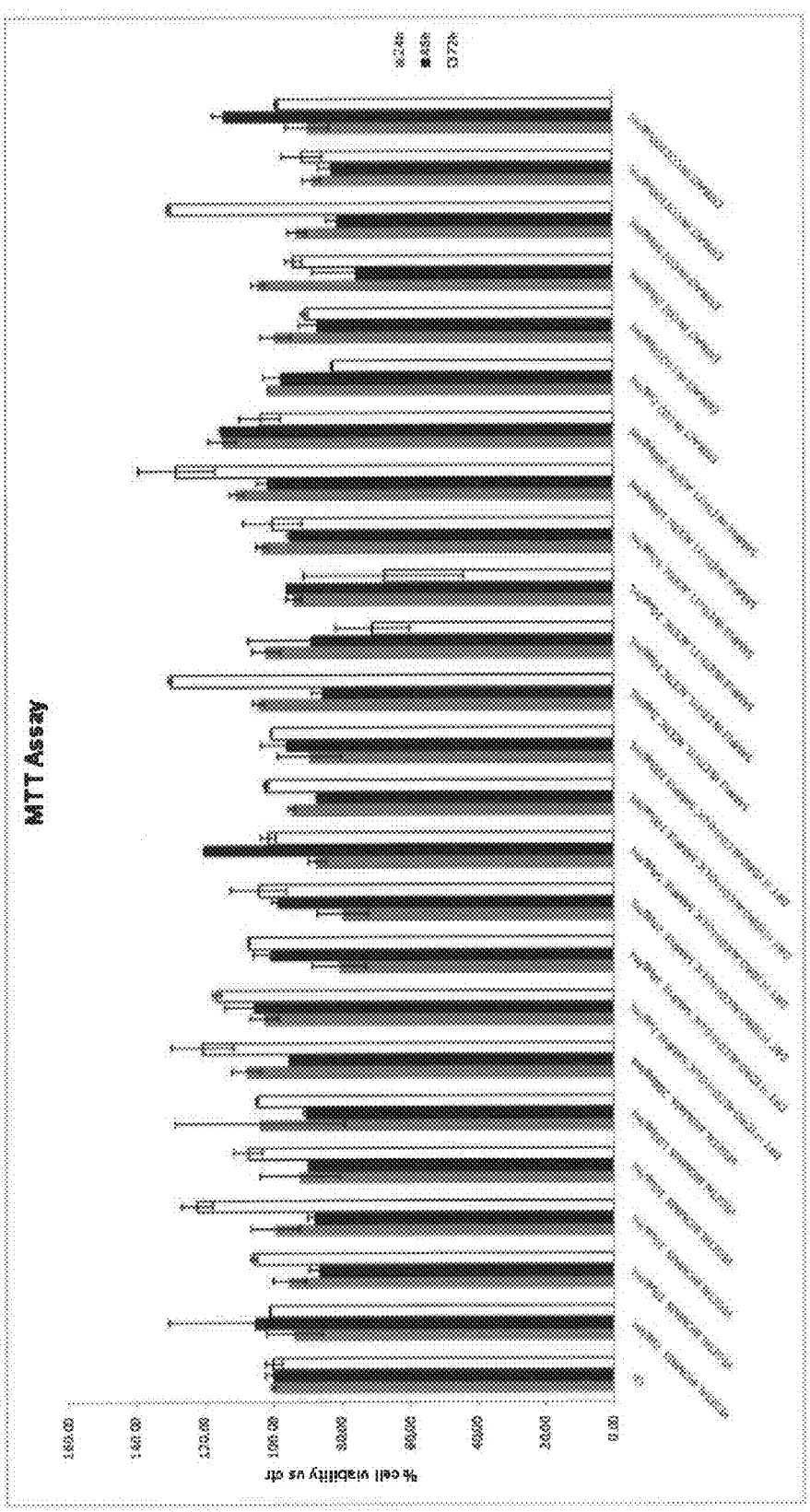
FIG. 1 shows bar graphs relating to the cytotoxicity data obtained by the MTT assay of Example 8 on samples: vegetal biomass, hydroalcoholic extract of *Galeopsis segetum*, ethyl acetic extract of *Galeopsis segetum*, extract in supercritical $CO_2$ of *Galeopsis segetum*, within the dose range 2-200 µg/ml for 24, 48 and 72 hours.

The Applicant has found that the vegetal extract of *Galeopsis segetum* Necker, when administered locally or cutaneously, performs a stimulating action on the follicle cells, reactivating the life cycle of the hair follicles.

Furthermore, it has surprisingly been found that the trichological activity of the extract of *Galeopsis segetum* Necker is also exerted on the quiescent hair bulbs of the scalp, typically present in those areas of the scalp wherein a thinning of the hair is found.

In accordance with a first aspect of the invention, therefore, there is provided the use of a vegetal extract from the plant of *Galeopsis segetum* Necker for stimulating the physiological growth of hair.

In accordance with a second aspect, there is provided a vegetal extract from the plant of *Galeopsis segetum* Necker for use in stimulating the physiological growth of hair.

The plant from which the vegetal extract at the basis of the invention derives is *Galeopsis segetum* Necker (*G. ochroleuca* Lam., *G. dubia* Leers, *G. villosa* Huds. also known as Downy Hemp Nettle), a herbaceous upright species with typical labiate flowers, belonging to the Lamiaceae family.

A vegetal extract for the uses of the invention may be derived from the roots, leaves, fruits or flowers of the plant of *Galeopsis segetum* Necker or from two or more of these parts of the plant.

In some embodiments, the vegetal extract is derived from the aerial part of the plant of *Galeopsis segetum* Necker.

According to some embodiments, the vegetal extract of the invention is obtained by extraction from a part of the plant, in particular the aerial parts or its vegetal tissue, using as an extraction means a physiologically acceptable or edible solvent. The term edible means a physiologically acceptable solvent that may be absorbed by the human body.

A suitable solvent to obtain the vegetal extract is a physiologically acceptable and/or edible liquid wherein the biologically active components are soluble and wherein they do not undergo alteration that deprives them of their activity.

In some embodiments the solvent is hydrophilic and is selected from water, ethyl acetate, ethanol or mixtures thereof.

In order to obtain the vegetal extract of plant of *Galeopsis segetum* Necker, extraction techniques may be employed using supercritical $CO_2$ or solid-liquid techniques suitable for separating/extracting from the vegetal tissues of the plant one or more biologically active components to restore physiological conditions of activity of the hair bulb.

In certain embodiments, the extraction of one or more biologically active components takes place by maceration of a vegetal portion or matrix of *Galeopsis segetum* Necker in a suitable solvent, for example a hydroalcoholic mixture.

For example, a vegetal portion or matrix, typically aerial parts, of the plant of *Galeopsis segetum* Necker is immersed in a suitable solvent for example a water-ethanol mixture, for a time suitable for enriching the solvent of one or more biologically active components. In these conditions, the extraction in the solvent of the biologically active components present in the vegetal tissues of the plant takes place by diffusion and osmosis.

Typically during maceration the matrix of plant of *Galeopsis segetum* Necker is contacted with the solvent for a variable time to obtain the extraction of an effective amount of biologically active component. In certain embodiments the maceration time may vary from 1 to 48 hours.

In certain embodiments the vegetal extract of *Galeopsis segetum* Necker is administered at a concentration from 0.01 to 100 mg/ml.

In accordance with certain embodiments the preparation of a suitable extract of *Galeopsis segetum* Necker comprises the following steps:

grinding a portion of the plant, for example the aerial parts, adding an extraction solvent, for example to obtain a drug/hydroalcoholic solvent weight ratio comprised between about 1:10 and about 1:50, macerating, extracting, filtering, concentrating the filtrate for example at a reduced pressure by evaporation of the solvent, optionally continuing the evaporation until eliminating the solvent optionally drying the extract.

In certain embodiments the extraction step may be repeated two or three times, until depleting the material to be extracted.

In the final step of removing the solvent by evaporation a solid carrier may be optionally added, such as, as a non-limiting example, starches or maltodextrins, to obtain the extract in the form of dry powder.

In accordance with another embodiment, the extraction method from *Galeopsis segetum* Necker comprises the following steps:

grinding for the example the aerial parts of the plant transferring the powder obtained in a suitable percolator.

leaching out for example with an amount of extraction solvent so as to have a drug/solvent weight ratio from about 1:20 to about 1:100 recirculating part of the leachate until depleting the material to be extracted pressing the vegetal bed extracted for recovering all the extraction solvent filtering the leachate concentrating the filtrate for example at a reduced pressure by evaporation of the solvent optionally continuing the evaporation until eliminating the solvent optionally drying the extract.

According to some embodiments, in the final step of removing the solvent by evaporation a solid carrier is added, for example a starch or maltodextrins, to obtain the extract in the form of dry powder.

Typically the extract obtained may be fluid, soft or dry. For example, in the fluid extract 1 ml extract contains biologically active components soluble in 1 g vegetal drug, in the soft extract the solved is partially evaporated in particular until the extract wets a filter paper, in the dry extract the solvent is evaporated almost completely to obtain a powder.

It is possible to prepare extracts of *Galeopsis segetum* having different polarity. For example it is possible to obtain a high-polarity extract using a polar solvent such as a hydroalcoholic solution, an intermediate-polarity extract using a less polar solvent such as ethyl acetate or a non-polar extract using supercritical $CO_2$. The preferred extraction techniques are those with high-polarity solvent and that with supercritical $CO_2$. In particular, with these techniques a fraction of the phytocomplex is extracted efficiently which performs an inhibitory activity towards the 5-alpha-reductase enzyme, which plays an important role in androgenetic alopecia and is a target of finasteride, a known compound having antiandrogenetic activity, effective in stimulating hair growth and in reactivating the physiological cycle of hair follicles.

In certain embodiments, the extraction is carried out using a weight ratio between solvent and vegetal matrix comprised between 1:10 and 10:1.

Further methods for obtaining the vegetal extract of the invention include extraction techniques by digestion, infusion, squeezing, decoction, leaching, counter-current extraction, soxhlet, extraction with supercritical gases or ultrasounds.

In some embodiments, the biologically active component contained in the extract of *Galeopsis segetum* Necker comprises at least one flavonoid, in particular, selected from the group comprising hypolaetin 4'-methyl ether 7-(2"-allosyl) glucoside monoacetylated, hypolaetin 4'-methyl ether 7-(2"-allosyl) glucoside diacetylated, isoscutellarein 7-(2"-allosyl) glucoside monoacetylated, hypolaetin 4'-methyl ether 7-(2"-allosyl) glucoside, hypolaetin 7-(2"-allosyl) glucoside monoacetylated, isoscutellarein 7-(2"-allosyl) glucoside and hypolaetin 7-(2"-allosyl) glucoside diacetylated.

The applicant has found that flavonoids particularly active for stimulating the activity of the hair bulb are hypolaetin 4'-methyl ether 7-(2"-allosyl)glucoside monoacetylated and/or hypolaetin 4'-methyl ether 7-(2"-allosyl)glucoside diacetylated.

In some embodiments, the compositions of the invention have a content of vegetal extract of *Galeopsis segetum* Necker comprised between 0.01 and 10% w/w, for example 3% w/w.

The biologically active components contained in the vegetal extract of the invention reactivate the life cycle of hair follicles, even when quiescent, of the scalp in thinned areas and/or areas affected by baldness. This action translates into the re-growth of hair also in areas of the scalp where the hair are thinned out. In accordance with a third aspect, the present invention provides the use of a composition comprising a vegetal extract of *Galeopsis segetum* Necker and a physiologically acceptable carrier in the treatment and/or prevention of hair loss or for stimulating the physiological growth of hair.

In accordance with a fourth aspect, a composition is provided comprising a vegetal extract of *Galeopsis segetum* Necker and a physiologically acceptable carrier for use in the treatment or prevention of hair loss.

In particular, the composition of the invention comprises an active amount of one or more biologically active components extracted from the plant of *Galeopsis segetum* Necker.

Typically the composition of the invention is a medical device, a pharmaceutical formulation, a dietary or nutritional supplement, or a cosmetic.

The composition of the invention, when administered locally or systemically, increases the viability of follicle cells, both in the anagen phase and in the miniaturization phase and reactivates quiescent cells of the scalp by regenerating the follicles and stimulating the growth of new hair.

In some embodiments the composition of the invention comprises a physiologically and/or pharmaceutically acceptable carrier, diluent or excipient.

Typically, the physiologically acceptable carrier of the composition of the invention is an excipient, carrier or diluent suitable for topical application and/or oral administration.

Within the scope of the present document, the term "carrier" relates to an excipient, carrier, diluent or adjuvant that may be present in the composition of the invention. Any carrier and/or excipient suitable for the form of preparation desired for administration is contemplated in the uses of the vegetal extract or herein described active ingredients present therein.

Typically, the composition of the invention uses components of a vegetal origin which are biologically active and substantially free from side effects, when administered orally or locally.

In some embodiments, the composition of the invention is administered orally. In other embodiments, the composition is applied to the skin, and in particular to the scalp.

The physiologically and/or pharmaceutically acceptable carrier, diluent or excipient may be selected based on the route of administration for which the resulting pharmaceutical composition is intended.

In some embodiments, the route of administration of the composition of the invention is topical. In these cases, the composition of the invention may be applied, in an effective amount, directly to the scalp.

For example, in the treatment of androgenetic alopecia a cosmetically active amount of composition of the invention may be applied directly to the scalp once or multiple times a day conveniently for cycles lasting 2-3 months, alternating with rest periods.

According to another aspect of the invention, there is provided a method of cosmetic treatment which comprises the application to the scalp of an effective amount of a composition of the type described previously.

The composition for topical application may be in the solid, semi-solid or fluid form. Suitable formulations in the solid form include creams, gels, pastes, ointments.

In other embodiments the formulation for local administration is in the fluid form, for example in the form of lotions, gels, shampoos, suspensions, emulsions.

In the case of formulations in the fluid or semi-fluid form, the vegetal extract may be diluted in a carrier in the physiologically acceptable liquid form such as water, alcohol, hydroalcoholic or glyceric solution or mixed with other liquids suitable for local application.

By way of example, the compositions of the invention in the liquid form may be prepared dissolving the biologically active components of the extract in water and/or alcohol. The liquid composition may be buffered to achieve a pH range conveniently selected between 5 and 7 so as to be compatible with the pH of the scalp and then be filtered and packaged in suitable containers such as vials or ampoules.

In some embodiments, the compositions of the invention may comprise excipients commonly used in the formulation of cosmetic or pharmaceutical preparations, for local use, such as preservatives, bactericidal agents, stabilizing agents, emulsifying agents, buffers, wetting agents, coloring agents and other excipients commonly used in the cosmetic/pharmaceutical preparation techniques.

In one embodiment, the formulation for local application is in the form of an emulsion containing the extract carried in a suitable excipient.

By way of example, suitable excipients are cellulose derivatives such as hydroxymethyl cellulose, hydroxypropyl methylcellulose, methylcellulose, hydroxypropyl cellulose, hydroxyethyl cellulose, carboxyethyl cellulose, ethylhydroxyethyl cellulose, cellulose acetate butyrate, cellulose acetate phthalate, and mixtures thereof.

Further examples of suitable excipients comprise the polymers belonging to the family of lactams, such as pyrrolidone and derivatives thereof, for example polyvinylpyrrolidone, polyvinylpolypyrrolidone and mixtures thereof, inorganic salts such as calcium or dicalcium phosphate, lubricants such as for example magnesium stearate, triacylglycerols and mixtures thereof.

In some embodiments, the composition for topical application comprises an excipient of the type hydroxymethyl cellulose and/or gelling agents with HLB suitable for the formulation and substances.

According to other embodiments, the administration of the composition of the invention takes place orally.

The compositions for oral administration may be in the solid or liquid form. Typical compositions in the solid form comprise tablets, capsules, powders, granules, pills. Typical compositions in the liquid form comprise solutions, emulsions, suspensions, syrups. All the compositions also comprise controlled-release forms of the same.

Tablets generally comprise a suitable carrier or excipient wherein the vegetal extract is dispersed, typically in the dry form.

The biologically active components of the composition of the invention may be present in variable amounts, for example comprised between 0.0001% by weight and 10% by weight, typically between 00.1 and 5% by weight.

In accordance with certain embodiments, the composition of the invention further comprises one or more active substances, such as vitamins, minerals, micronutrients and other substances active in stimulating the activity of the hair follicle.

In accordance with some embodiments, the composition for oral administration is a functional food, a nutraceutical composition, a dietary product, a supplement or a nutritional product or a medical device.

Functional food means any modified food or food ingredient which may provide a benefit or protection against a drawback or a physiological condition, besides the traditional nutrients it contains.

Nutraceutical product means a product isolated or purified from edible substances. A nutraceutical product is such when it shows to have a physiological advantage or to provide protection against a drawback or physiological disorder.

Dietary or nutritional supplement means a product containing a vitamin, mineral, vegetal extract, amino acid, metabolite, extract, concentrate or mixtures of these ingredients.

The amount administered and the frequency of administration of the composition will depend on the type and severity of the trichological condition to be treated.

The composition of the invention is effective in preventing and/or treating the forms of baldness or hair thinning, such as for example defluvium and androgenetic alopecia.

The present invention shall now be described with reference to the following examples which are provided for illustration purposes and shall not be intended as limiting of the scope of the present invention.

EXAMPLE 1

| Tablet for oral use | |
|---|---|
| *Galeopsis segetum* dry extract | 100-300 mg |
| Micro-crystalline cellulose | 80-340 mg |
| Calcium phosphate dibasic dihydrate | 50-100 mg |
| Colloidal silica | 2.5-10 mg |
| Magnesium stearate | 2.5-10 mg |
| PEG-4000 | 0.5-2.5 mg |
| Cross-linked sodium carboxymethyl cellulose | 0.25-0.5 mg |
| Sodium alginate | 0.25-0.5 mg |
| Hydroxy-propyl-methylcellulose | 0.25-0.5 mg |

EXAMPLE 2

| Granular product for oral use | |
| --- | --- |
| Erythritol | 20-40% w/w |
| *Galeopsis segetum* dry extract | 0.5-4% w/w |
| Mannitol | 10-30% w/w |
| Flavoring agent | 5-10% p/p |
| Sucralose | 0.1-0.3% p/p |
| Starch as needed to | 100 |

EXAMPLE 3

| Tablet for oral use | |
| --- | --- |
| Refined sucrose | 50-90 mg |
| *Galeopsis Segetum* soft extract | 50-100 mg |
| Talc | 10-20 mg |
| Maize starch | 5-25 mg |
| Powdered sugar | 5-15 mg |
| 70% non-crystallizable sorbitol | 5-10 mg |
| Magnesium stearate | 1-3 mg |
| Arabic gum | 2-3 mg |
| Titanium dioxide | 1-2.5 mg |
| Gelatin | 1-3 mg |
| Type A copolymer of methacrylic acid | 1-2.5 mg |
| Light magnesium carbonate | 0.5-1 mg |
| Polyethylene glycol 6000 | 0.1-0.3 mg |
| Dibutyl phthalate | 0.1-0.25 mg |
| Methyl paraoxybenzoate | 0.01-0.03 mg |
| Micro-crystalline cellulose as needed to | 300 mg |

EXAMPLE 4

| Lotion for application to hair and scalp | |
| --- | --- |
| Type C denatured ethyl alcohol | 500-1500 mg |
| *Galeopsis Segetum* fluid extract | 50-300 mg |
| Polyoxyethylenated Hydrogenated castor oil | 12.2-48.8 mg |
| Fragrance | 3-12 mg |
| Disodium EDTA dihydrate | 1.5-6 mg |
| Water as needed to | 5 ml |

EXAMPLE 5

| Treatment Shampoo | |
| --- | --- |
| Zetesol MGS | 30-50% w/v |
| Protelan LS 9011 | 5-15% w/v |
| Mirasheen CP 820/G | 2-6% w/v |
| Rewoderm LI S 80 | 2-4% w/v |
| BC 2262 | 0.5-1.5% w/v |
| Cocamide MIPA | 0.5-1.5% w/v |
| Protelan AG 11 | 0.5-1.5% w/v |
| Citric acid | 0.5-1.5% w/v |
| Fragrance | 0.5-1.5% w/v |
| Sodium hydroxymethylglycinate | 0.5-1.5% w/v |
| Betaine | 0.25-0.75% w/v |
| Lauryl methyl gluceth-10 hydroxypropyldimonium chloride | 0.25-0.75% w/v |
| Polyquaternium-10 | 0.2-0.6% w/v |
| Tetra sodium EDTA | 0.1-0.3% w/v |
| Panthenol | 0.1-0.3% w/v |
| *Galeopsis Segetum* fluid extract | 0.05-1.0% w/v |

-continued

| Treatment Shampoo | |
| --- | --- |
| Butyl hydroxyanisole (BHA) | 0.005-0.02% p/v |
| Water as needed to | 100 ml |

EXAMPLE 6

| Cutaneous emulsion | |
| --- | --- |
| Propylene glycol | 6-8 g |
| Glyceryl stearate palmitate | 3-5 g |
| Coconut oil | 2-4 g |
| Cetostearyl alcohol (25) OE | 1-3 g |
| Emulsifying wax | 1-3 g |
| Benzyl alcohol | 0.5-1.5 g |
| *Galeopsis Segetum* soft extract | 0.5-1.5 g |
| Cetyl alcohol (6) OE | 0.25-1.0 g |
| Water as needed to | 100 g |

EXAMPLE 7

The proliferative effects of the extract of *Galeopsis segetum* have been studied in HFDPC-c (PromoCell®) cells maintained in culture in the presence of Follicle Dermal Papilla Growth Medium, and following the instructions of the manufacturer (PromoCell®).

The proliferative activity was assessed by means of an MTT assay.

The MTT assay (3-(4,5-dimethylthiazol-2-yl)-2,5-diphenyltetrazolium) is a colorimetric assay used to assess in vitro cell proliferation [Mosmann T, 1983], since it allows to measure the cell proliferation and viability by the assessment of the mitochondrial activity. This method is very useful to measure cell growth following treatment with mitogens, antigenic stimuli, growth factors and for cytotoxicity studies.

The assay provides for the use of a chromogenic oxidizing agent, MTT, consisting of a polycyclic system ($C_{18}H_{16}BrN_5S$) provided with a tetrazolic ring which may be easily reduced by mitochondrial dehydrogenases or by other electron transport systems, forming, by opening the tetrazolic ring, a nitrogenous chromogenic compound designated as formazan. Such formazan forms insoluble crystals in the intracellular environment, to which the membranes are substantially impermeable: the entry of the molecule to the cell is therefore allowed, but the exit of the product is not if this has been correctly metabolized, that is if the electron transport chains are still metabolically active.

Formazan crystals are then solubilized in dimethylsulfoxide (DMSO), thus causing the solution to shift from yellow to dark blue-violet.

The HFDPC-c cells were seeded at a density of $5*10^4$ cells/well in 96-well plates. After 24 hours, once a confluence of about 80% was achieved, the cells were treated with 6 increasing concentrations of extract of *Galeopsis segetum* N.: 0.01; 0.05; 0.1; 0.5; 1 and 2 mg/mL in whole medium. The control cells, on the other hand, were maintained in culture in whole medium.

The plates were incubated at 37° C., under 5% $CO_2$ for 24 hours, at the end of this the culture medium was replaced with a 100 µL solution of MTT (Sigma-Aldrich, St. Louis, Mo., USA) 0.5 mg/mL in whole culture medium.

After 3 hours of incubation at 37° C., the medium was collected and the formazan crystals were solubilized with 100 µL per well of DMSO (Sigma-Aldrich, St. Louis, Mo., USA). The plate, coated with aluminum, was placed in a mechanical stirrer (Arhos 160—PBI International, Milan, Italy) at 120 rpm for 15 minutes at room temperature.

The absorbance of the stained solution was measured by means of a microplate spectrophotometric reader (BioTek Instruments Inc., Bad Frieddrichshall, Germany) at a wavelength of 570 nm (reference wavelength at 630 nm).

The data were expressed as the percentage of cell viability as compared to the control cells (ctr), according to the following formula:

% cell viability/ctr=(Abs sample/Abs ctr)*100

All the assays were performed in duplicate.

The test results show a dose-dependent increase in cell proliferation indicating a stimulus of cell growth of follicle cells.

Stem cells of the hair follicle play an important role in the hair cycle, but it is known that with ageing there occurs a loss of the same and of the capability to restore hair regeneration. From stem cells, the matrix cells are formed, whose growth and differentiation are under the influence of substances produced by the cells of the dermal papilla. The secretory activity of the dermal papilla is under the control of substances produced by cells of the spinous layer of the outer sheath of the root or by hormones. In fact, the cells of the spinous layer produce peptides greater than 3000 Daltons capable of causing a two- to five-fold increase of the number of mitoses of cells of the papilla. Recently it has been found that the fibroblast growth factor (bFGF) and the platelet-derived growth factor (PDGF) enhance the growth of cells of the dermal papilla. In particular, these proteins increase the synthesis of stromelysin (an enzyme, metalloproteinase) acting on the cells of the papilla and speeding up the growth thereof. The cells of the dermal papilla produce numerous cytokines which affect the proliferation of cells of the hair matrix. Accordingly, an effect, such that exerted by the extract of *Galeopsis*, stimulating the growth of these cells is advantageous in promoting hair growth.

EXAMPLE 8

Object of the Experimental Work

The experimental procedure reported hereinafter has as an object studying the in vitro activity of different samples of *Galeopsis segetum*, subjected to different extraction processes, in order to characterize the anti-oxidant activity and the activity of stimulating hair growth thereof.

Materials

| Assayed samples | | | | |
|---|---|---|---|---|
| | INTERNAL NAME | | | |
| | A | C | D | E |
| UNIQUE IDENTIFYING NAME | VEGETAL BIOMASS | DRY HYDRO-ALCOHOLIC SAMPLE | SAMPLE IN ETHYL ACETIC | EXTRACT IN CO2 |
| LOT | Lot C/181286 | Lot 921/30/D | Lot 921/30/G | Lot 522/14/23/A |
| STORAGE | R.T. | R.T. | R.T. | R.T. |

| Assayed samples | | | | |
|---|---|---|---|---|
| | INTERNAL NAME | | | |
| | A | C | D | E |
| CONCENTRATIONS | 2-10-20-50-100-200 µg/mL | 2-10-20-50-100-200 µg/mL | 2-10-20-50-100-200 µg/mL | 2-10-20-50-100-200 µg/mL |

All the extracts were diluted 100 mg/ml in DMSO and filtered in sterile conditions. Stocks were stored at −20° C.

| Reagents and equipment used | |
|---|---|
| | SUPPLIER |
| REAGENTS | |
| 30% Hydrogen peroxide | SIGMA, 216763 |
| Agarose (For routine use) | SIGMA, A9539-100 G |
| Calf Bovine Serum | ATCC, 30-2030 |
| 2',7'-Dichloro-fluorescin diacetate | SIGMA, 35845 |
| Dimethylsulfoxide | SIGMA, D2438-50 ML |
| Dulbecco's Modified Eagle's Medium | ATCC, 30-2002-500 ml |
| Dulbecco's Phosphate Buffered Saline | SIGMA, D8537 |
| Ethidium bromide solution (10 mg/mL, for molecular biology, aqueous solution) | SIGMA, E1510 |
| Gel Loading Buffer | SIGMA, G2526 |
| RNAse, none detected | |
| High Capacity cDNA Reverse Transcription Kit, 200 Reactions | APPLIED BYOSISTEMS, 4368814 |
| Mesenchymal Stem cell medium | INNOPROT, P60115 |
| MTT | SIGMA- Aldrich, M2128 |
| Penicillin-Streptomycin | SIGMA, P0781 |
| PreMix Ex Taq | TAKARA, RR039A |
| Primary cell detach kit | INNOPROT, P60305 |
| TaqMan ® Gene Expression Assays for SRD5A1 Mm00614213ml | APPLIED BYOSISTEMS, 4331182 |
| TaqMan ® Gene Expression Assays for SRD5A2 Mm00446421ml | APPLIED BYOSISTEMS, 4331182 |
| TaqMan ® Gene Expression Assays for pactin Mm00466519ml | APPLIED BYOSISTEMS, 4331182 |
| Testosterone | SIGMA, 86500 |
| Trypsin-EDTA solution | SIGMA, T3924 |
| a-tocopherol | SIGMA, T3251 |
| GeneAllRibospin mini 50 | Gene-all, 304-150 |
| Human Keratin, type II cytoskeletal 6A(KRT6A) ELISA kit 96T | CSB-EL012561HU |
| Film for ELISAplate | Starlab (E2796-9793) |
| 96 well plate for ELISA assay (NUNC MAXI SORP) | Sigma (M9410, Sigma) |
| Cellytic M | SIGMA, C2978 |
| Protease Inhibitor Cocktail | SIGMA, T1500 |
| EQUIPMENT | |
| Spectrophotometer (MOD: 6715, BS-6715B0) | Jenway UV/VIS |
| 15 L digital water bath from +5° C. to +100° C. (Mod: Swbd1, BS-SWB2D) | Stuart |
| Balance (Mod. XS204) | Mettler Toledo |
| Laminar flow cabinet (Mod: Gemini) + UV lamp with anti-reflex equipment | Steril Manifacturing Division |
| HeraCell CO$_2$ incubator (Mod: 150 ADV) | ThermoScientific |
| 85° C. horizontal freezer ULT130, 120 L (Mod: Labfrost, MME-TE21140) | Elcold |
| Bürker counting chamber w/clamps (DI-DA-443/3) | Carlo Erba |
| Microplate autoreader (EL 808) | Biotek |
| Vortex | Arhos160-PBI International |
| Fluoroskan Ascent FL | Thermo Fisher |
| Microplate Fluorescence Reader | Scientific Inc., Waltham, MA |

Biological Models Used

Cultures of Murine Embryonic Fibroblasts

The immortalized line of murine embryonic fibroblasts BALB/c3T3, Clone A31 (ATCC, Manassas, Va., USA), was obtained from the Istituto Nazionale di Ricerca sul Cancro (Genova, Italy).

The cells were maintained in culture in 25 cm3 sterile flasks and incubated at 37° C. in a humid atmosphere under 5% $CO_2$. As the culture medium DMEM (Dulbecco's Modified Eagle's Medium, ATCC, Manassas, Va., USA) was used added to 10% fetal calf serum (FCS), 1% non-essential amino acids (NEAA), a 1% penicillin and streptomycin mixture (Pen-Strep Mix). These latter reagents were all purchased from Lonza, Inc. (Barcelona, Spain)

During the culture step, the 1:3 split was performed every 2 days, upon reaching 80% confluence, by washing with 1×PBS (Lonza, Barcelona, Spain) and detachment of the cells with a trypsin-EDTA solution (Lonza, Barcelona, Spain) at 37° C. for 2 minutes.

| | |
|---|---|
| ICLC CATALOGUE CODE | CCL-163 ™ |
| FILER | Aaronson S. |
| BIBLIOGRAPHIC REFERENCES | 10993-5:1999. Aaronson S A, Todaro G J. Development of 3T3-like lines from Balb-c mouse embryo cultures: transformation susceptibility to SV40. J. Cell. Physiol. 72: 141-148, 1968. PubMed: 4301006 |
| | Todaro G J, Aaronson S A. Properties of clonal lines of murine sarcoma virus transformed Balb-3T3 cells. Virology 38: 174-202, 1969. PubMed: 4306523 |
| | Aaronson S A, Todaro G J. Basis for the acquisition of malignant potential by mouse cells cultivated in vitro. Science 162: 1024-1026, 1968. PubMed: 4301647 |
| | Jainchill J L, Todaro G J. Stimulation of cell growth in vitro by serum with and without growth factor. Relation to contact inhibition and viral transformation. Exp. Cell Res. 59: 137-146, 1970. PubMed: 4194429 |
| | Thompson S A, et al. COOH-terminal extended recombinant amphiregulin with bioactivity comparable with naturally derived growth factor. J. Biol. Chem. 271: 17927-17931, 1996. PubMed: 8663535 |
| | Anderson M T, et al. Simultaneous fluorescence-activated cell sorter analysis of two distinct transcriptional elements within a single cell using engineered green fluorescent proteins. Proc. Natl. Acad. Sci. USA 93: 8508-8511, 1996. PubMed: 8710900 |
| | Biological evaluation of medical devices. Part 5: Tests for in vitro cytotoxicity. Sydney, NSW, Australia: Standards Australia; Standards Australia AS ISO 10993.5-2002. |
| | Biological evaluation of medical devices--Part 5: Tests for in vitro cytotoxicity. Geneva (Switzerland): International Organization for Standardization/ANSI; ISO ISO |

Cell Cultures of Human Hair Follicle Outer Root Sheath Cells

The Human Hair Follicle Outer Root Sheath Cells (HHFORSC) provided by Innoprot were isolated by Scien Cell Research Labs from the hair outer root sheath. The cell line was cultured in the medium for mesenchymal stem cells (MSCM): 500 ml basal medium, 10% fetal bovine serum (FBS), 1% mesenchymal stem cells growth supplement (MSCGS), 1% penicillin/streptomycin solution (P/S solution) and maintained in 25 $cm^2$ culture flasks at 37° C. and under 5% $CO_2$.

Before proceeding by plating the cells, the flask had to be coated with poly-L-lysine (2 μg/$cm^2$).

Every two days the confluent cultures were split at 1:3-1:6, after washing with DPBS (Dulbecco's Phosphate-Buffered Saline), using the T/E solution (trypsin/EDTA solution) and TNS (Trypsin Neutralization Solution) and seeded at 2-5×$10^4$ cell/$cm^2$, 37° C., 5% $CO_2$.

Controls

MTT Assay (BALB3T3)

Positive Control:

Non-treated cells in DMEM medium with (Dulbecco's Modified Eagle's Medium, ATCC, Manassas, Va., USA) added to 10% fetal bovine serum (FCS), 1% non-essential amino acids (NEAA), a 1% penicillin and streptomycin mixture (Pen-Strep Mix), and maintained in 25 $cm^2$ (96 well) culture plates at 37° C. and under 5% $CO_2$.

DCFH-DA Assay and MTT-Induced Oxidative Stress Test (BALB3T3) Negative Control:

Non-treated cells in DMEM medium (Dulbecco's Modified Eagle's Medium, ATCC, Manassas, Va., USA) added to 2.5% fetal bovine serum (FCS), 1% non-essential amino acids (NEAA), a 1% penicillin and streptomycin mixture (Pen-Strep Mix), and maintained in 25 $cm^2$ (96 well) culture plates at 37° C. and under 5% $CO_2$.

Positive Control:

Cells treated for 2 hrs with 1 mM hydrogen peroxide in DMEM medium (Dulbecco's Modified Eagle's Medium, ATCC, Manassas, Va., USA) added to 2.5% fetal bovine serum (FCS), 1% non-essential amino acids (NEAA), a 1% penicillin and streptomycin mixture (Pen-Strep Mix), and maintained in 25 $cm^2$ (96 well) culture plates at 37° C. and under 5% $CO_2$ (in the dark).

Study of the Activity of Induction of 5-Alpha Reductase (BALB3T3)

Negative Control:

Non-treated cells in DMEM medium (Dulbecco's Modified Eagle's Medium, ATCC, Manassas, Va., USA) added to 10% fetal bovine serum (FCS), 1% non-essential amino acids (NEAA), a 1% penicillin and streptomycin mixture (Pen-Strep Mix) and 10 ng/mL Testosterone, and maintained in 25 $cm^2$ (12 well) culture plates at 37° C. and under 5% $CO_2$.

Positive Control:

Cells treated for 24 hrs with finasteride (0.05 mg/mL) in DMEM medium (Dulbecco's Modified Eagle's Medium, ATCC, Manassas, Va., USA) added to 10% fetal bovine serum (FCS), 1% non-essential amino acids (NEAA), a 1% penicillin and streptomycin mixture (Pen-Strep Mix) and 10 ng/mL Testosterone, and maintained in 25 $cm^2$ (12 well) culture plates at 37° C. and under 5% $CO_2$.

Study of Expression of Keratin 6A (ORS)

Negative Control:

Non-treated cells in MSCM, 10% fetal bovine serum (FBS), 1% mesenchymal stem cells growth supplement (MSCGS), 1% penicillin/streptomycin solution (P/S solution) and maintained in 25 $cm^2$ (12 well) culture plates at 37° C. and under 5% $CO_2$.

Before proceeding by plating the cells, the flask had to be coated with poly-L-lysine (2 μg/$cm^2$).

Methods

Preliminary Cytotoxicity Assay (MTT Assay)-BALB3T3

Method Principle

The MTT assay (3-(4,5-dimethylthiazol-2-yl)-2,5-diphenyltetrazolium) is a colorimetric assay used to assess in vitro cell proliferation, since it allows to measure the cell proliferation and viability by the assessment of the mitochondrial activity. This method is very useful to measure cell growth following treatment with mitogens, antigenic stimuli, growth factors and for cytotoxicity studies.

The assay provides for the use of a chromogenic oxidizing agent, MTT, consisting of a polycyclic system ($C_{18}H_{16}BrN_5S$) provided with a tetrazolic ring which may be easily reduced by mitochondrial dehydrogenases or by other electron transport systems, forming, by opening the tetrazolic ring, a nitrogenous chromogenic compound designated as formazan. Formazan forms insoluble crystals in the intracellular environment, to which the membranes are substantially impermeable: the entry of the molecule to the cell is therefore allowed, but the exit of the product is not if this has been correctly metabolized, that is if the electron transport chains are still metabolically active.

Formazan crystals are then solubilized in dimethylsulfoxide (DMSO), thus causing the solution to shift from yellow to dark blue-violet.

Experimental Procedure

The assay was conducted following the Mosmann (1983) method, with some small modifications. The BALB3T3 cells were seeded at a density of $5*10^4$ cells/well in 96-well plates. After 24 hours, once a confluence of about 80% was achieved, the cells were treated with 6 different increasing concentrations of the extracts of *Galeopsis segetum* (vegetal biomass; dry hydroalcoholic sample; sample in ethyl acetic; extract in $CO_2$) 2-10-20-50-100-200 mg/mL in whole medium. The control cells, on the other hand, were maintained in culture in whole medium.

The plates were incubated at 37° C., under 5% $CO_2$ for 24, 48 and 72 hours. At the end of all the treatments, the medium was collected and replaced with 100 μL of a 0.5 mg/mL MTT solution (Sigma-Aldrich, St. Louis, Mo., USA) in whole culture medium.

After 3 hours of incubation at 37° C., the medium was collected and the formazan crystals were solubilized with 100 μL per well of DMSO (Sigma-Aldrich, St. Louis, Mo., USA). The plate, coated with aluminum, was placed in a mechanical stirrer (Arhos 160—PBI International, Milan, Italy) at 120 rpm for 15 minutes at room temperature.

The absorbance of the stained solution was measured by means of a microplate spectrophotometric reader (BioTek Instruments Inc., Bad Frieddrichshall, Germany) at a wavelength of 570 nm (reference wavelength at 630 nm).

The data were expressed as the percentage of cell viability as compared to the control cells (ctr), according to the following formula:

% cell viability/ctr=(Abs sample/Abs ctr)*100

All the assays were performed at least twice in duplicate.

MTT with Induced Oxidative Stress-BALB3T3

Method Principle

The murine fibroblasts BALB3T3 represent one of the validated models for studying oxidative stress in vitro (Subirade et al., 1995; Kutuk et al., 2004).

Studies conducted in 2005 by Rajapakse and colleagues (2005) have highlighted the possibility of employing a widely used and versatile method such that of the MTT essay for studying the in vitro anti-oxidant activity of active compounds. Specifically, by this method it is possible to study the protecting effects of such compounds on cells subsequently subjected to oxidative stress. The induction of oxidative stress is performed by means of incubation with hydrogen peroxide, an inducing agent of the production of oxidative damage in cells by the formation of ROSs. The possible protecting effects may be determined by the assessment of the post-oxidative stress cell viability of cells pre-treated/pre-exposed to the active compounds to be tested, in comparison to cells subjected to the same oxidative stress. Greater cellular viability will correspond to a protecting effect of the compounds tested.

Experimental Procedure

The assay was conducted according to the method described by Coda and colleagues (Coda et al., 2012), with some modifications.

The murine fibroblasts BALB3T3 were seeded in a 96-well plate at a density of $5*10^4$ cells/well and incubated at 37° C., under 5% $CO_2$, until reaching about 80% confluence.

Subsequently, the cells were incubated for 16 hours with the extracts of *Galeopsis segetum* (vegetal biomass; dry hydroalcoholic sample; sample in ethyl acetic; extract in $CO_2$) at the following concentrations: 20-50 and 100 μg/mL.

The dilutions were prepared starting from 1000× stock in DMSO, filtered in sterile conditions and using DMEM medium added to 2.5% fetal calf serum (FCS), 1% non-essential amino acids (NEAA), a 1% penicillin and streptomycin mixture (Pen-Strep Mix).

Cells treated with 1 mM $H_2O_2$ were used as the positive control; cells maintained in the culture medium alone (DMEM 2.5% FCS), on the other hand, were used as the negative control.

At the end of the 16 hour pre-treatment, the cells were washed with 1×PBS and incubated for 90 minutes with a 1 mM $H_2O_2$ solution (Sigma-Aldrich, St. Louis, Mo., USA) in serum-free medium, in the dark, at 37° C. and 5% $CO_2$.

Once the induction step of the oxidative stress was ended, the assessment of cell viability was performed of the various samples, according to the method described in section 4.1.2 (MTT assay).

The data were expressed as the percentage of cell viability as compared to the non-stressed control cells (ctr), according to the following formula:

cell viability/ctr=(Abs sample/Abs ctr)*100

All the assays were performed at least twice in duplicate.

Study of the Effects of Extracts of *Galeopsis segetum* on ROS Production by Means of the DCFH-DA Assay-BALB3T3

Method Principle

The ROS production in the cell line of murine fibroblasts BALB3T3 was determined via spectrofluorimetry by means of the assay of 2,7-dichlorofluorescin-diacetate (DCFH-DA), as described by Tobi and colleagues (Tobi et al., 2000). DCFH-DA is a non-fluorescent compound in its lipophilic form, capable of diffusing through the cellular membrane. Once inside the cell, it is deacetylated by intracellular esterases to reduced 2,7-dichlorofluorescin (DCFH), which is also non-fluorescent. DCFH, being incapable of crossing the cellular membrane again, consequently accumulates in the cells (Curtin et al., 2002). The reaction with intracellular ROSs leads to the oxidation of DCFH to 2,7-dichorofluorescin (DCF), a highly fluorescent compound. The intensity of such fluorescence may be detected with a fluorimeter, allowing estimating the amount of ROSs produced in the cells.

Experimental Procedure

The protocol used for this experiment represents a modified version of that described in a work by Tobi and colleagues (Tobi et al., 2000).

The murine fibroblasts BALB3T3 were seeded in 96-well plates at a density of $5*10^4$ cells/well and incubated until reaching about 80% confluence.

Subsequently, the cells were incubated for 16 hours with the extracts of *Galeopsis segetum* (vegetal biomass; dry hydroalcoholic sample; sample in ethyl acetic; extract in $CO_2$) at the following concentrations: 20-50 and 100 µg/mL. The dilutions were prepared starting from 1000× stock in DMSO, filtered in sterile conditions and using DMEM medium added to 2.5% fetal calf serum (FCS), 1% non-essential amino acids (NEAA), a 1% penicillin and streptomycin mixture (Pen-Strep Mix).

Cells treated with 1 mM $H_2O_2$ were used as the positive control; cells maintained in the culture medium alone (DMEM 2.5% FCS), on the other hand, were used as the negative control.

α-Tocopherol, tested at the concentration of 25-50-250-500 µM;

At the end of incubation, the induction of oxidative stress was carried out, by 90 minute treatment with a 4 mM $H_2O_2$ solution, in the dark, at 37° C. and 5% $CO_2$. Once the treatment was ended, the cells were washed twice with 1×PBS and lysed with CelLytic™ lysis buffer (Sigma-Aldrich, St. Louis, Mo., USA) according to the provider's protocol.

Subsequently, the lysates were transferred to a black 96-well plate and the DCF fluorescence was spectrofluorometrically read using a FluoroskanAscent FL Microplate Fluorescence Reader (Thermo Fisher Scientific Inc., Waltham, Mass., USA), with excitation and emission wavelengths of 485 and 538 nm, respectively. The emission values (RFU) obtained for each sample, related to the intracellular ROS production, were compared to the emission value obtained for the negative control (ctr, cells treated with 1 mM $H_2O_2$) and expressed as percentage of ROS produced according to the following equation:

$$\% \text{ ROS produced/ctr} = (Abs538 \text{ nm sample}/Abs538 \text{ nm ctr}) \ast 100$$

All the assays were performed at least twice in duplicate.

Study of the Effects of Extracts of *Galeopsis segetum* on the Activity of 5 Alpha Reductase (Isoform2)-BALB3T3

Experimental Procedure

The gene expression of the isoform 2 of 5 alpha-reductase (SRD5A2) in cells BALB3T3 was assessed by quantitative RT-PCR (quantitative reverse transcription polymerase chain reaction—qRT-PCR).

This analysis had 3 sequential steps:
extraction of total RNA;
reverse transcription in cDNA;
qRT-PCR.

The murine fibroblasts BALB3T3 were seeded in 12-well plates at a density of $0.5 \ast 10^6$ cells/well and incubated until reaching about 80% confluence.

Subsequently, the cells were incubated for 24 hours with the extracts of *Galeopsis segetum* (vegetal biomass; dry hydroalcoholic sample; sample in ethyl acetic; extract in $CO_2$) at the following concentrations: 20-50 and 100 µg/mL. The dilutions were prepared starting from 1000× stock in DMSO, filtered in sterile conditions and using DMEM medium added to 10% fetal calf serum (FCS), 1% non-essential amino acids (NEAA), a 1% penicillin and streptomycin mixture (Pen-Strep Mix).

Cells maintained in culture medium alone (DMEM 2.5% FCS), on the other hand, were used as the negative control.

Finasteride, selective inhibitor of the isoform 2 (SRD5A2) of 5 alpha reductase, was tested at the concentration of 0.05 mg/mL.

At the end of the incubation, the RNA extraction was performed,

The total RNA was extracted from the cells BALB3T3 by using the Ribospin™ commercial kit (Gene All Biotechnology Co., LTD)

At the end of the incubation with the active compounds of interest, the cells were washed with PBS (1×) and lastly subjected to the RNA extraction procedure. At the end of the extraction, by using a spectrophotometer (Jenway UV/VIS MOD: 6715, BS-6715B0), the concentrations were calculated in µg/mL of total RNA extracted at the wavelength of 260 nm.

Finally, the integrity of RNA (2 µg/mL) was assessed by an electrophoretic run on 1% agarose gel.

The total RNA was converted to cDNA (complementary DNA), using an enzyme capable of synthesizing a DNA molecule using an RNA strand as a template; this RNA-dependent DNA polymerase enzyme takes the name of reverse transcriptase.

This binds to the 3' end of a single RNA strand and by means of random primers and deoxynucleotide triphosphate (DNTP) synthesizes the cDNA strand.

To this end, a "PrimeScript™ RT Reagent Kit (perfect Real Time)" (TakaraBioInc., Japan) was used containing 5× PrimeScript Buffer (for real Time); PrimeScript RT Enzyme Mix1; OligodTPrimer; Random 6 mers; RNAse free dH2O.

The RNA extracted and quantified was diluted at a concentration of 2 µg/mL and reverse-transcribed to cDNA. A 10 µL Master Mix was prepared (containing 5× PrimeScript Buffer (for real Time); PrimeScript RT Enzyme Mix1; OligodTPrimer 50 µM; Random 6 mers 100 µM) to which 10 µL RNA were added (2 µg/mL).

The samples were placed in a thermal cycler (Stratagene Mx3000P Real Time PCR System, Agilent Technologies Italia S.p.A., Milan, Italy) and subjected to reverse transcription under the following conditions:
37° C. for 15 minutes;
85° C. for 5 seconds;
4° C. hold.

At the end of reverse transcription the samples were supplemented with 30 µL DEPC water to obtain a final concentration of cDNA of 40 ng/µL.

qRT-PCR is a method for amplifying and quantifying in real time the amplicons produced monitoring the fluorescence emitted during the reaction.

For the RT-PCR amplification the TaqMan® probe system (Applied Biosystems) was used. The following TaqMan probes were used: Mm00446421 ml (SDR5A2) and Mm00466519 ml (β-actin). As the control gene (housekeeping) β-actin was used.

The Taqman probe is a type of probe allowing developing fluorescence upon advancing the amplification. At its 5' end there is bound a reporter (fluorophore FAM™), while at the 3' end there is a quencher. The proximity between the reporter and the quencher cancels the emission of the fluorescence signal. With the 5' exonuclease activity of the thermally stable DNA polymerase (Taq polymerase) fluorescence is detected and the accumulation of amplification products may be assessed by increasing the fluorescence of the reporter that increases at each run.

For qRT-PCR a Master Mix was arranged as follows:
10 µL "2× Premix Ex Taq";
1 µL "20× TaqMan Gene ExpressionAssays" (containing 2 primers and fluorophore FAM™-tagged fluorescence probe);
0.4 µL passive reference Rox II;
5 µL DEPC water.

The Master Mix was supplement with 4 µL cDNA for the target gene and 1 µL cDNA for the housekeeping gene.

Amplification was conducted under the following conditions for 40 runs:
95° C., 30 sec (Amplitaqactivation);
95° C., 5 sec (Denaturation);
60° C., 20 sec (Annealing—extension);
Each analysis was conducted in duplicate.

The data obtained were analyzed according to the $2^{-\Delta\Delta Ct}$ method, and it was therefore possible to calculate the values regarding the expression of the gene of interest, normalized with respect to the housekeeping gene and calibrated on the control sample (non-treated cells):

$\Delta\Delta Ct = \Delta Ct_{target\text{-}housekeeping}(\text{controllo}) - \Delta Ct_{target\text{-}housekeeping}(\text{cellule trattate})$ Assuming an amplification efficiency of 100%, the $2^{-\Delta\Delta Ct}$ was calculated.

Study of the Effects of Extracts of *Galeopsis segetum* on the Expression of Cytokeratin 6A-ORS Experimental Procedure For the study of the expression of cytokeratin 6A in ORS cells a commercial kit was used: Human Keratin, type II cytoskeletal 6A(KRT6A) ELISA kit 96T (CSB).

Day 1:
When the cells (HHFORSC) reached about 80% confluence, they were detached with trypsin/EDTA and seeded at a density of $1 \times 10^6$ cells/ml in 12-well plates and then incubated at 37° C., 5% $CO_2$ (24 h).

Day 2:
When the cells reached about 80% confluence, they were exposed to active compounds to be tested: vegetal biomass; dry hydroalcoholic sample; sample in ethyl acetic; extract in $CO_2$, at the following concentrations: 20-50 and 100 μg/mL. The dilutions were prepared starting from 1000× stock in DMSO, filtered in sterile conditions and using Mesenchymal Stem Cells Medium.

Day 3:
At the end of the incubation the cells were lysed by using Cell Lytic™ lysis buffer supplemented at 1% with protease inhibitor Cocktail and the lysates were used for the ELISA assay.

In order to normalize the expression of the protein on the total content of proteins in the sample, the amount of total protein in each sample was assessed by Bradford assay (Bradford, 1976).

Results

The results obtained by the experimentation are illustrated in the appended FIGS. 1-5 which show the following:

5.1 Preliminary Cytotoxicity Assay (MTT Assay)-BALB3T3

FIG. 1 shows the data obtained by the MTT assay (mean±SD) In the test the extracts of *Galeopsis segetum* dry extract (vegetal biomass), the hydroalcoholic extract (dry hydroalcoholic sample), the extract in ethyl acetic (sample in ethyl acetic) and the extract in $CO_2$ (extract in $CO_2$) were assessed in the dose range 2-200 μg/ml for 24, 48 and 72 hours. The results show that all the compounds tested are not cytotoxic.

5.2 MTT with Induced Oxidative Stress-BALB3T3

Figure 2:
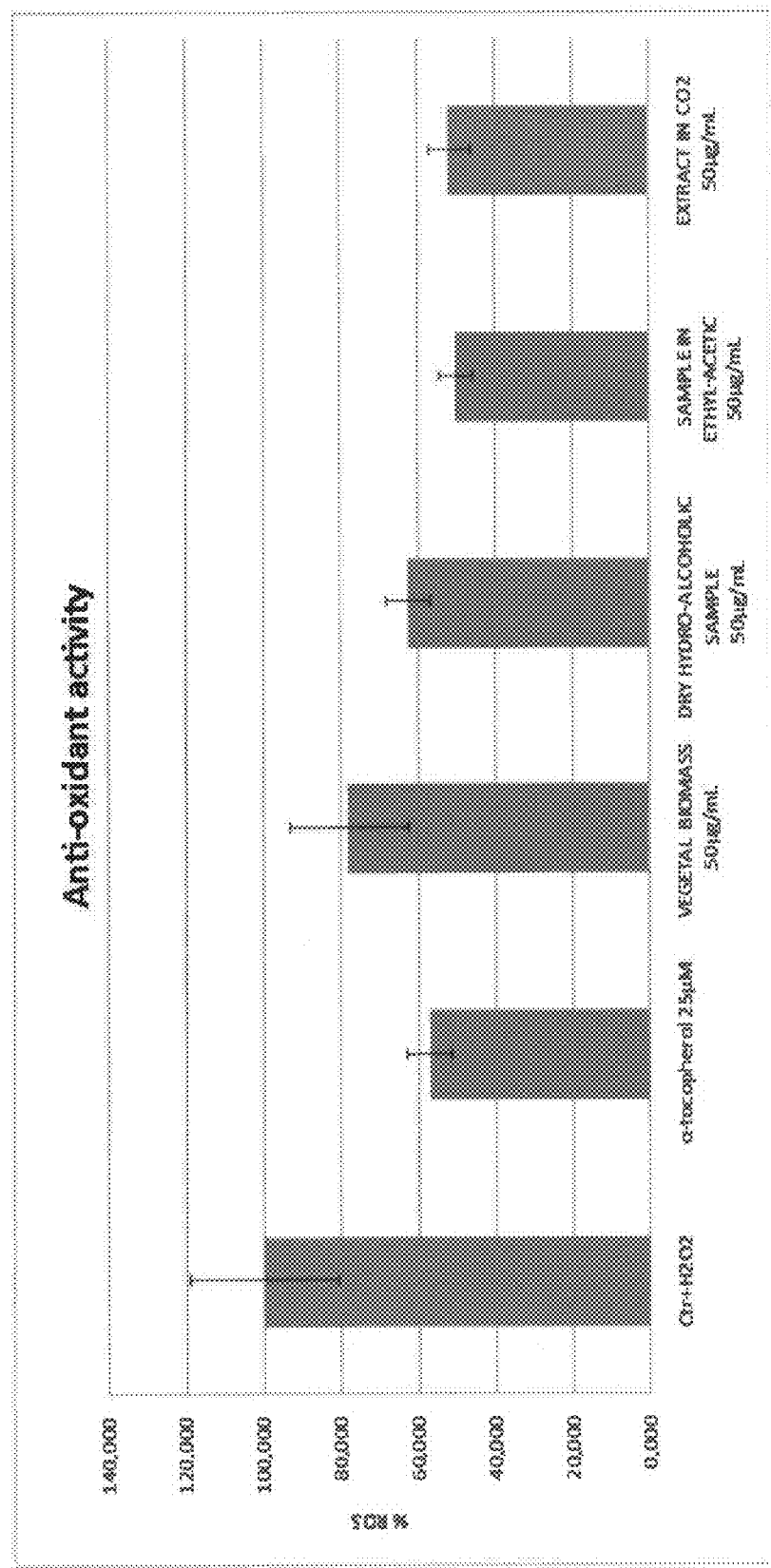
FIG. 2 shows bar graphs reporting the results of the MTT assay with oxidative stress induced on samples of α-tocopherol, vegetal biomass, hydroalcoholic extract, ethyl acetic extract and extract with supercritical $CO_2$ of *Galeopsis segetum*, as reported in Table 1 of Example 8.

FIG. 2 shows the results of the MTT experimentation with oxidative stress induced on the samples indicated in the following Table 1.

| Samples | Scavenger activity |
|---|---|
| α-tocopherol 25 μM | 43.10 |
| VEGETAL BIOMASS 50 μg/mL | 22.14 |
| DRY HYDROALCOHOLIC SAMPLE 50 μg/mL | 37.64 |
| SAMPLE IN ETHYL ACETIC 50 μg/mL | 50.13 |
| EXTRACT IN CO2 50 μg/mL | 48.58 |

Specifically, FIG. 2 shows the anti-oxidant activity of the vegetal biomass, hydroalcoholic extract, ethyl acetic extract, extract in $CO_2$, while Table 2 shows the data of the scavenger activity.

The results show how the extracts express anti-oxidant activity. It is shown how the extraction processes determine an improvement of such activity, especially the extraction in ethyl acetic and $CO_2$. If the scavenger activity of the vegetal biomass (22.14) is considered, this is improved following hydroalcoholic extraction (37.64; +70%) and increasingly with ethyl acetic and $CO_2$ extraction (50.13 and 48.58, respectively; on average +123%).

5.3 Study of the Effects of Extracts of *Galeopsis segetum* on ROS Production by Means of the DCFH-DA Assay-BALB3T3

Figure 3:
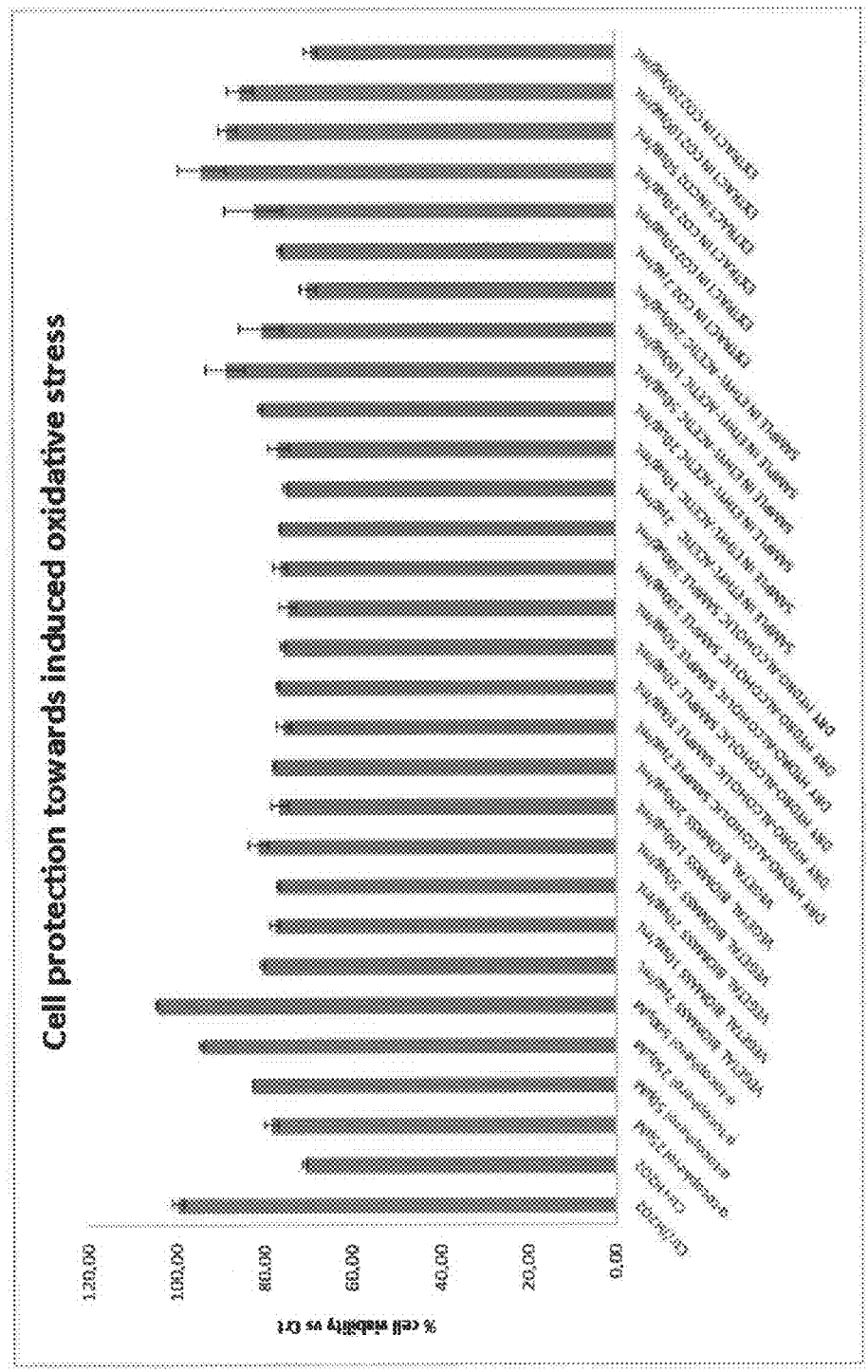
FIG. 3 shows bar graphs representing the data on the production of intracellular ROSs by the assay of Example 8 of samples represented by α-tocopherol, vegetal biomass and hydroalcoholic extract, ethyl acetic extract and extract with supercritical $CO_2$ from *Galeopsis segetum*.

The data for the cell protection activity towards oxidative stress induced by $H_2O_2$ are shown in FIG. 3.

The induced oxidative stress produces a situation of cell suffering which leads to a significant loss of cell population. The treatment with the compounds (vegetal biomass, hydroalcoholic extract, ethyl acetic extract, extract in $CO_2$) show a protecting capability towards the apoptotic process induced by oxidative stress. Such activity is in line with what has been observed for anti-oxidant activity and is relevant for ethyl acetic and $CO_2$ extracts.

5.4 Study of the Effects of Extracts of *Galeopsis segetum* on the Activity of 5 Alpha Reductase (Isoform2)-BALB3T3

Figure 4:
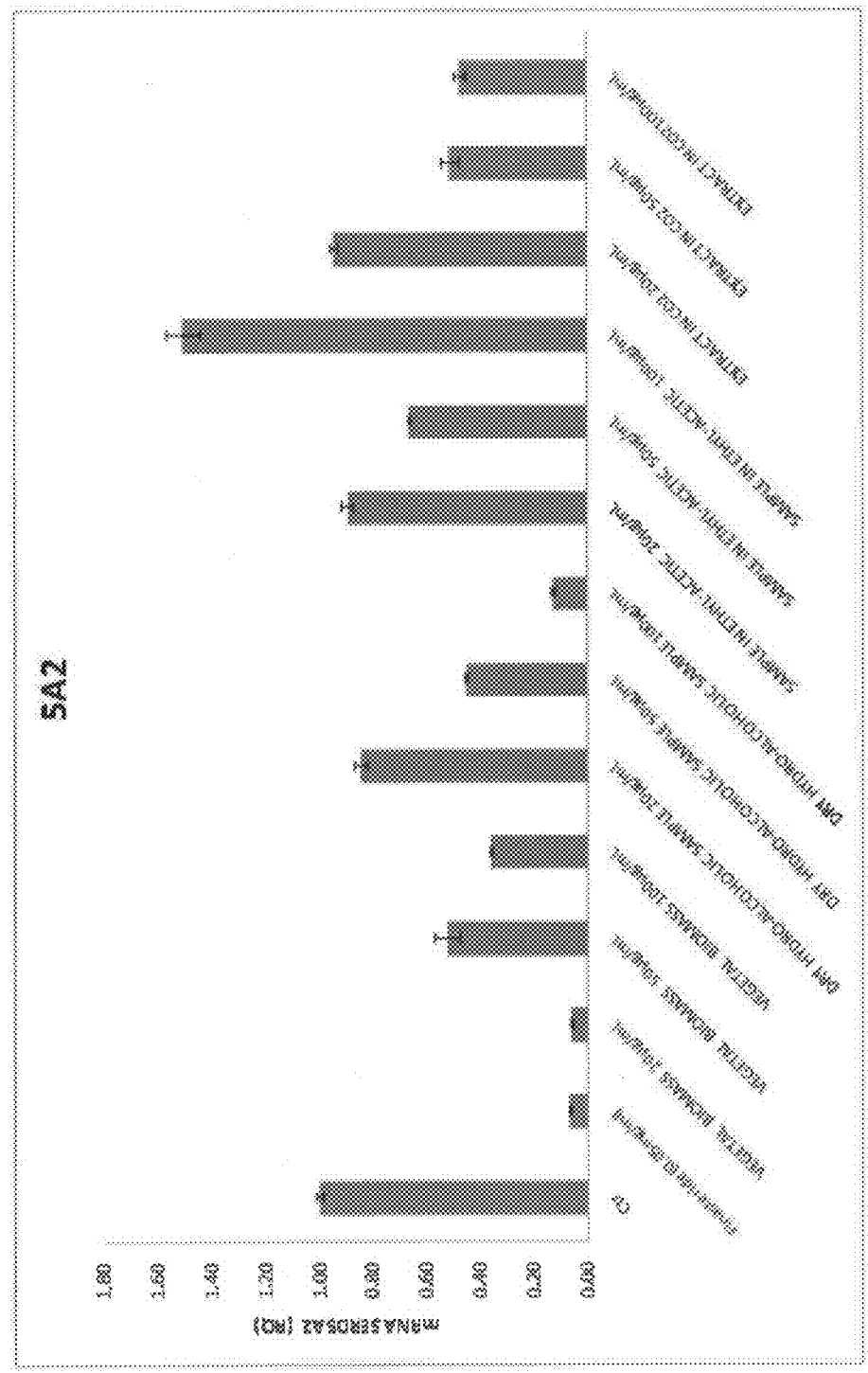
FIG. 4 shows bar graphs representing the effects on activity of the isoform 2 of 5-alpha-reductase, of samples of α-tocopherol, vegetal biomass and hydroalcoholic extract, ethyl acetic extract and extract with supercritical $CO_2$ of *Galeopsis segetum*, as reported in Example 8.

FIG. 4 shows the data of gene expression of the isoform 2 of 5 alpha-reductase, target of Finasteride.

*Galeopsis segetum* (vegetal biomass) shows an inhibitory activity towards 5 alpha-reductase type2. Also the hydroalcoholic and $CO_2$ extracts (50 and 100 μg/ml) show such activity, while it is less apparent in ethyl acetic extraction.

Figure 5:
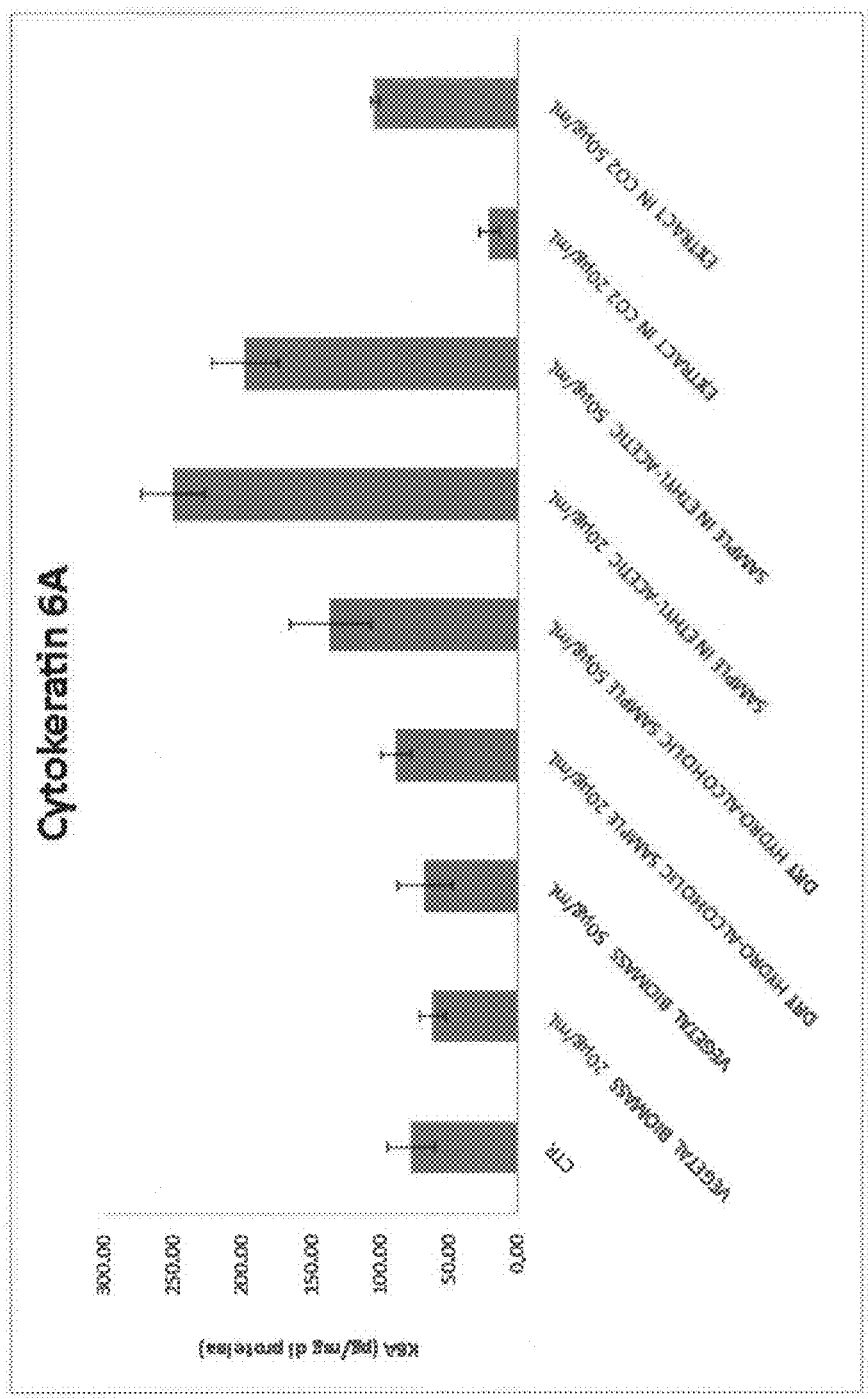
FIG. 5 shows bar graphs representing the effects on the expression of cytokeratin 6A of two concentrations per each of vegetal biomass, hydroalcoholic extract of *Galeopsis segetum*, ethyl acetic extract of *Galeopsis segetum*, extract in $CO_2$ supercritical of *Galeopsis segetum*, as reported in Example 8.

5.5 Study of the Effects of Extracts of *Galeopsis segetum* on the Expression of Cytokeratin 6A-ORS FIG. 5 shows the values relating to cytokeratin 6A, a well-known marker of follicle stem cells wherein it plays an important role for homeostasis and hair growth.

The data obtained show that vegetal biomass is not capable of stimulating such keratin, while the samples obtained with the hydroalcoholic and ethyl acetic extraction (at both doses tested) and extraction in $CO_2$ (only the larger dose) are capable of stimulating it.

The stimulus extent of such keratin by the ethyl acetic sample is significant.

Conclusion

The tests carried out have shown:
absence of cytotoxicity of all the samples tested in the range 2-200 microg/ml up to 72 h of cell treatment (fibroblasts) (MTT assay)
good anti-oxidant activity of all compounds, it should be noted that the extractions improve the anti-oxidant activity. As compared to the vegetal biomass, the hydroalcoholic extraction improves such activity by +70%, while the ethyl acetic and CO$_2$ extraction by 123% (dicholorofluorescin assay).

such activity is also reflected in the cell protection following induced oxidative stress (test on fibroblasts)

the test on the stimulus of synthesizing cytokeratin 6A by ORS (follicle cells Outer Root Sheath) sets forth that the vegetal biomass is not capable of stimulating the synthesis thereof, while hydroalcoholic, ethyl acetic and CO$_2$ extractions (in this case only at the larger dose tested) induce the synthesis of such keratin.

EXAMPLE 9

Introduction

The present example relates to the preparation of three extracts having different polarity obtained from the aerial parts of *Galeopsis segetum*. The most polar one was prepared by extraction with aqueous ethanol. Initially, a screening of the solvents was performed, in order to identify the most suitable alcoholic content. Using supercritical CO$_2$, a non-polar extract was prepared.

An extract having intermediate polarity was prepared extracting the less polar components of the hydroethanolic extract with ethyl acetate.

These extracts were used for screening the activity.

1. OBJECT OF THE TESTS

Preparation of three extracts having different polarity obtained from the aerial parts of *Galeopsis segetum*, and characterization thereof.

The following extracts were prepared:
Dry hydroalcoholic extract of *Galeopsis segetum*—IDN6764
Dry extract with ethyl acetate of *Galeopsis segetum*—IDN 6765
Extract with CO$_2$ of *Galeopsis segetum*—IDN 6766

2. EXPERIMENTAL STEP 2.1 Biomass

All the work referred to in the present document was carried out on the aerial parts of *Galeopsis segetum* CoA 1054/9394.

2.2 Hydroalcoholic Extract: Screening of Ethanol Content

In order to find the best extraction solvent in terms of yield, features and secondary metabolite pattern by TLC, screening with different ethanol content was performed, namely 20%, 40% and 70%. For each test, 20 g biomass of medium was suspended in 400 ml solvent at 50° C., mixing for 4 hours. The suspensions were filtered and the solutions concentrated until dryness.

Each extract was assessed with respect to the extraction yield, features and TLC. The results are shown in Table 1

TABLE 1

| Sample | Extraction solvent | Yield of dry extract | Features | TLC# (Rf of main stains 0.57 and 0.80) |
|---|---|---|---|---|
| 921/28/A | 20% EtOH | 14.8% | Brown powder | Intensity lower than 921/28/B and 921/28/C |
| 921/28/B | 40% EtOH | 12.0% | Brown powder | Similar to 921/28/C |
| 921/28/C | 70% EtOH | 13.1% | Tacky greenish powder | Similar to 921/28/B |

The comparison of the intensities of stains was carried out at the same concentration (5%).

According to the TLC, the best extraction solvents are 40% and 70% EtOH. On the other hand, this latter extract contains more chlorophyll which gives rise to a greenish and tacky extract. For this reason, as the extraction solvent in §40% EtOH was selected.

2.3 Preparation of Dry Hydroalcoholic Extract of *Galeopsis segetum*—IDN6764 (Ref. Test 921/30/D)

a) 100 g of ground aerial parts of *Galeopsis segetum*, CofA 1054/9394, were poured into a percolator, covered with 0.54 l 40% ethanol, heated to 50° C. and left in static conditions for 4 h.

Once discharge was performed, three further extractions were performed (3×0.3 l), using the same temperature and the same contact time.

b) The leachates were collected and concentrated under vacuum in order to obtain a suspension of about 0.15 l and a 10% dry residue.

c) The suspension was centrifuged to separate the insoluble residue and the clean solution was concentrated under vacuum until it was dry.

The residue was dried at 50° C. under vacuum for 24 h.

Yield: 14.79 g dry hydroalcoholic extract of *Galeopsis segetum*—IDN6764, lot 921/30/D, CofA 14/0605/LRE yield w/w: 14.79%

2.4 Preparation of Dry Extract with Ethyl Acetate of *Galeopsis segetum* IDN6765 (Ref. Test 921/30/G)

a) 850 g of ground aerial parts of *Galeopsis segetum*, CofA 1054/9394, were poured into a percolator, covered with 4.6 l 40% ethyl alcohol, heated to 50° C. and left in static conditions for 4 h.

Once discharge was performed, three further extractions were performed (4×2.5 l), maintaining the same temperature and the same contact time.

b) The leachates were collected and concentrated under vacuum in order to obtain a suspension of about 1.4 l and a 10% dry residue.

c) The suspension was centrifuged to separate the insoluble residue and the clean solution was subjected to extraction with ethyl acetate (3×0.35 l).

d) The organic phases were joined and concentrated until obtaining a soft bulk. Water was added (10 ml) and the suspension was concentrated again until obtaining a soft bulk. This treatment was repeated in order to remove any residual ethyl acetate.

Finally, the residue was dried at 50° C. under vacuum for 24 h.

Yield: 2.85 g dry extract with ethyl acetate of *Galeopsis segetum*—IDN6765, lot 921/30/G, CofA 14/0606/LRE yield w/w: 0.34%

2.5 Preparation of Extract of *Galeopsis segetum* with CO$_2$ IDN6766 a) 5 kg of ground aerial parts of *Galeopsis segetum*, CofA 1054/9394, were poured in the extractor's container. The extraction was performed in accordance with the following conditions:

Temperature, 55° C.
Pressure, 270-280 bar
$CO_2$ flow, 70 kg/h
Extraction time, 4.5 h
b) The extraction provides an emulsion (94 g). The emulsion was dried at 60° C. under vacuum for 4 h.
Yield: 74 g of extract of *Galeopsis segetum* with $CO_2$—IDN6766, lot 522/14/23A, CofA 14/0604/LRE.
yield w/w: 1.48%

3. RESULTS

Figure 8:
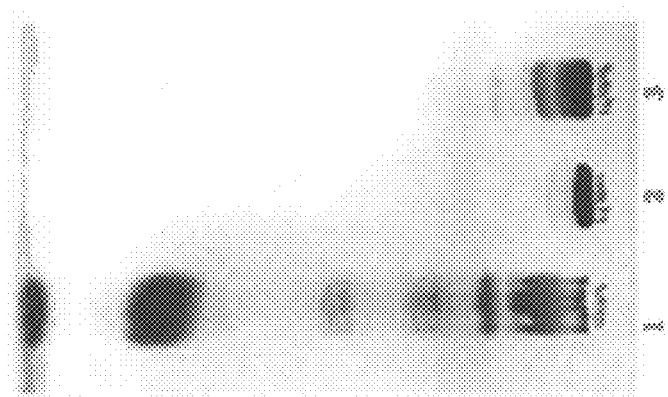
FIG. 8 shows the characterization data of the three extracts of *Galeopsis segetum* described in Example 9 by means of a TLC chromatography with high-polarity eluent.
Figure 7:
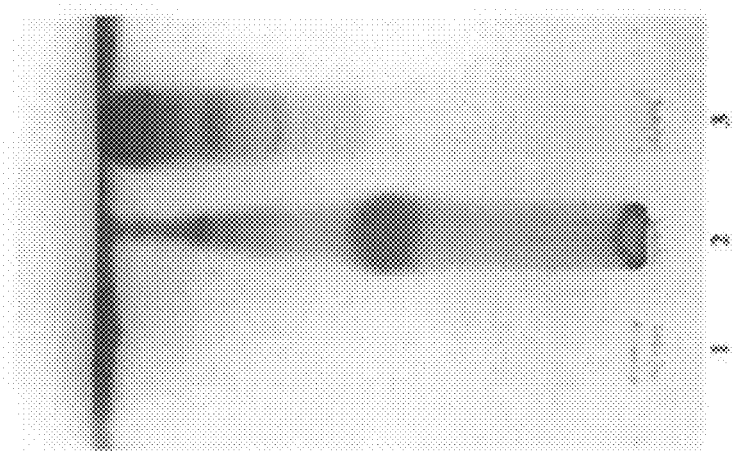
FIG. 7 shows the characterization data of the three extracts of *Galeopsis segetum* described in Example 9 by means of a TLC chromatography with high-polarity eluent.
Figure 11:
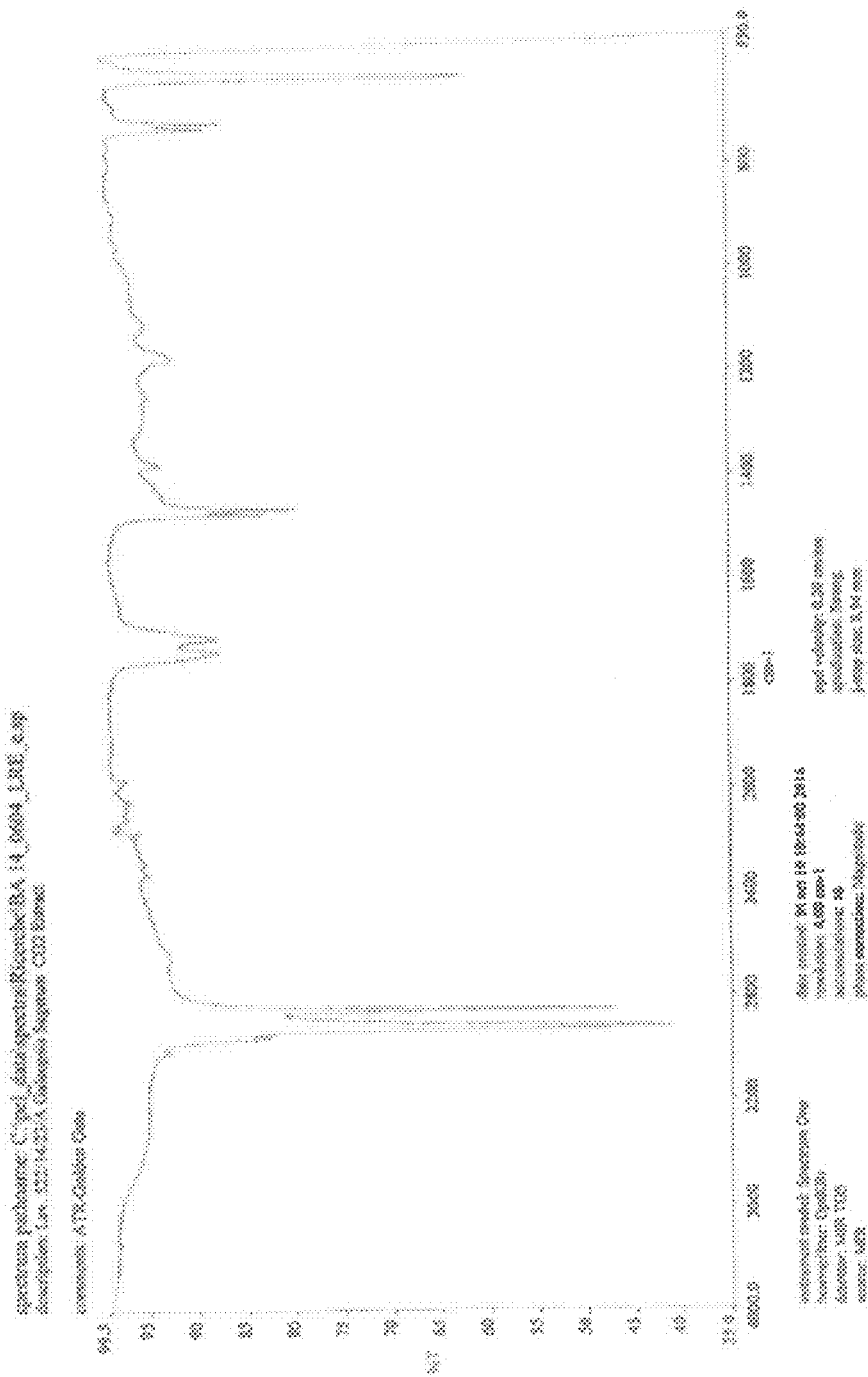
FIG. 11 shows a graph with FT-IR spectrum of the extract with supercritical $CO_2$ of *Galeopsis Segetum* of Example 9.

The extracts were characterized performing the following detections:
Appearance
Identification with TLC, as shown in the appended FIGS. 7 and 8
Identification with FT-IR, as shown in the appended FIGS. 9-11
The results are reported in Table 2

TABLE 2

| Sample | Appearance | Identification with TLC | Identification with FT-IR |
|---|---|---|---|
| Dry hydroalc. extract of *Galeopsis s.* lot 921/30/D, CofA 14/0605/LRE | Fine brown powder | Fixation 1 (high-polarity eluent) | Fixation 3 |
| Dry extract with ethyl acetate of *Galeopsis s.* lot 921/30/G, CofA 14/0606/LRE | Fine greenish powder | Fixation 2 (low-polarity eluent) | Fixation 4 |
| Extract with $CO_2$ of *Galeopsis s.* lot 522/14/23/A, CofA 14/0604/LRE | Pasty brown bulk | | Fixation 5 |

4. CONCLUSION

From the aerial parts of *Galeopsis segetum* three extracts having different polarity were prepared and characterized.

The invention claimed is:

1. A method for treating a human suffering from androgenetic alopecia or hair loss comprising administering a therapeutically effective amount of an extract of *Galeopsis segetum* Necker to the human suffering from androgenetic alopecia or hair loss to effectively treat said androgenetic alopecia or hair loss in said human.

2. The method of claim 1, wherein said extract is obtained by extracting of a portion of a *Galeopsis segetum* Necker plant with a physiologically acceptable solvent.

3. The method of claim 2, wherein said solvent is water, ethanol, a mixture of water and ethanol, or supercritical $CO_2$.

4. A method for treating a human suffering from androgenetic alopecia or hair loss comprising administering a therapeutically effective amount of a composition containing an extract from *Galeopsis segetum* Necker to the human suffering from androgenetic alopecia or hair loss to effectively treat said androgenetic alopecia or hair loss in said human.

5. The method according to claim 4, wherein the extract contains a flavonoid selected from the group consisting of monoacetylated hypolaetin 4'-methyl ether 7-(2"-allosyl) glucoside, diacetylated hypolaetin 4'-methyl ether 7-(2"-allosyl) glucoside, monoacetylated isoscutellarein 7-(2"-allosyl) glucoside, hypolaetin 4'-methyl ether 7-(2"-allosyl) glucoside, monoacetylated hypolaetin 7-(2"-allosyl) glucoside, isoscutellarein 7-(2"-allosyl) glucoside, diacetylated hypolaetin 7-(2"-allosyl) glucoside, and mixtures thereof.

6. The method according to claim 5, wherein said flavonoid is monoacetylated hypolaetin 4'-methyl ether 7-(2"-allosyl) glucoside, diacetylated hypolaetin 4'-methyl ether 7-(2"-allosyl) glucoside, or a mixture thereof.

7. The method according to claim 4, wherein said composition is administered orally or topically.

8. The method according to claim 4, wherein composition is in the form of a lotion, an emulsion, a shampoo, a cream or an ointment.

9. The method according to claim 4, wherein the composition is in the form of a tablet, a pill or a granulated powder.

10. The method according to claim 4, wherein the composition further comprises an ingredient selected from the group consisting of a vitamin, a mineral, a micronutrient, and mixtures thereof.

11. The method according to claim 4, wherein the composition is in the form of a nutraceutical, a functional food, a dietary supplement, a food supplement, a pharmaceutical product or a cosmetic product.

\* \* \* \* \*